United States Patent
Hresko et al.

(10) Patent No.: US 12,109,004 B2
(45) Date of Patent: Oct. 8, 2024

(54) REMOTE ACCESS FOR AMBULATORY MEDICAL DEVICE

(71) Applicant: ZOLL Medical Corporation, Chelmsford, MA (US)

(72) Inventors: Patrick Hresko, Mount Pleasant, PA (US); Trisha A. Biel, Glenshaw, PA (US); Zachary D. Mason, Verona, PA (US); Shane S. Volpe, Saltsburg, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 316 days.

(21) Appl. No.: 17/454,394

(22) Filed: Nov. 10, 2021

(65) Prior Publication Data
US 2022/0095919 A1 Mar. 31, 2022

Related U.S. Application Data

(63) Continuation of application No. 16/548,079, filed on Aug. 22, 2019, now Pat. No. 11,202,569, which is a
(Continued)

(51) Int. Cl.
*A61B 5/00* (2006.01)
*G16H 40/40* (2018.01)
(Continued)

(52) U.S. Cl.
CPC .......... *A61B 5/0015* (2013.01); *A61B 5/7475* (2013.01); *G16H 40/40* (2018.01);
(Continued)

(58) Field of Classification Search
CPC ......... A61B 5/0015; A61B 5/145; A61B 5/74; A61B 5/7475; G16H 40/40; G16H 40/63; G16H 40/67; G16H 80/00
See application file for complete search history.

(56) References Cited

U.S. PATENT DOCUMENTS 3,922,665 A 11/1975 Curry et al.
4,576,170 A 3/1986 Bradley et al.
(Continued)

FOREIGN PATENT DOCUMENTS

EP 707825 4/1996
EP 761255 3/1997
(Continued)

OTHER PUBLICATIONS

International Preliminary Report on Patentability for International Patent Application No. PCT/US2016/023057, mailed Oct. 5, 2017, 9 pages.
(Continued)

*Primary Examiner* — George Manuel
(74) *Attorney, Agent, or Firm* — Finch & Maloney PLLC

(57) ABSTRACT

An ambulatory medical device includes a sensor configured to acquire a signal indicative of a physiological condition of a patient, a controller operatively coupled to the sensor and configured to monitor the physiological signal, and to perform a diagnostic test, and a remote access manager operatively coupled to the controller and configured to monitor for a command from a remote system to perform the diagnostic test, and to cause the controller to perform the diagnostic test in response to the command. In the device, the remote access manager may be further configured to transmit data representing an operational status of the ambulatory medical device to the remote system. The operational status of the controller may result from performing the diagnostic test. The remote access manager may be further configured to send the data representing the operational status of the ambulatory medical device in real time or substantially in real time.

22 Claims, 12 Drawing Sheets

Related U.S. Application Data continuation of application No. 15/475,282, filed on Mar. 31, 2017, now Pat. No. 10,426,342.

(60) Provisional application No. 62/315,789, filed on Mar. 31, 2016.

(51) Int. Cl.
  *G16H 40/63*   (2018.01)
  *G16H 40/67*   (2018.01)
  *G16H 80/00*   (2018.01)
  *A61B 5/145*   (2006.01)

(52) U.S. Cl.
  CPC ............ *G16H 40/63* (2018.01); *G16H 40/67* (2018.01); *G16H 80/00* (2018.01); *A61B 5/145* (2013.01); *A61B 5/74* (2013.01)

(56) References Cited

U.S. PATENT DOCUMENTS

| | | | |
|---|---|---|---|
| 4,580,572 A | 4/1986 | Granek et al. |
| 4,583,547 A | 4/1986 | Granek et al. |
| 4,729,377 A | 3/1988 | Granek et al. |
| 4,928,690 A | 5/1990 | Heilman et al. |
| 4,991,217 A | 2/1991 | Garrett et al. |
| 5,078,134 A | 1/1992 | Heilman et al. |
| 5,348,008 A | 9/1994 | Bornn et al. |
| 5,371,692 A | 12/1994 | Draeger et al. |
| 5,381,798 A | 1/1995 | Burrows |
| 5,645,571 A | 7/1997 | Olson et al. |
| 5,741,306 A | 4/1998 | Glegyak et al. |
| 5,749,913 A | 5/1998 | Cole |
| 5,879,374 A | 3/1999 | Powers et al. |
| 5,899,925 A | 5/1999 | Ochs et al. |
| 5,919,212 A | 7/1999 | Olson et al. |
| 5,929,601 A | 7/1999 | Kaib et al. |
| 5,944,669 A | 8/1999 | Kaib |
| 6,065,154 A | 5/2000 | Hulings et al. |
| 6,097,982 A | 8/2000 | Glegyak et al. |
| 6,253,099 B1 | 6/2001 | Oskin et al. |
| 6,280,461 B1 | 8/2001 | Glegyak et al. |
| 6,304,780 B1 | 10/2001 | Owen et al. |
| 6,336,900 B1 | 1/2002 | Alleckson et al. |
| 6,374,138 B1 | 4/2002 | Owen et al. |
| 6,390,996 B1 | 5/2002 | Halperin et al. |
| 6,406,426 B1 | 6/2002 | Reuss et al. |
| 6,418,346 B1 | 7/2002 | Nelson et al. |
| 6,442,433 B1 | 8/2002 | Linberg |
| 6,546,285 B1 | 4/2003 | Owen et al. |
| 6,602,191 B2 | 8/2003 | Quy |
| 6,668,192 B1 | 12/2003 | Parker et al. |
| 6,681,003 B2 | 1/2004 | Linder et al. |
| 6,694,191 B2 | 2/2004 | Starkweather et al. |
| 6,804,554 B2 | 10/2004 | Ujhelyi et al. |
| 6,865,413 B2 | 3/2005 | Halperin et al. |
| 6,889,078 B2 | 5/2005 | Struble et al. |
| 6,889,079 B2 | 5/2005 | Bocek et al. |
| 6,908,437 B2 | 6/2005 | Bardy |
| 7,088,233 B2 | 8/2006 | Menard |
| 7,108,665 B2 | 9/2006 | Halperin et al. |
| 7,149,579 B1 | 12/2006 | Koh et al. |
| 7,220,235 B2 | 5/2007 | Geheb et al. |
| 7,295,871 B2 | 11/2007 | Halperin et al. |
| 7,340,296 B2 | 3/2008 | Stahmann et al. |
| 7,353,063 B2 | 4/2008 | Simms, Jr. |
| 7,439,705 B2 | 10/2008 | Koike |
| 7,453,354 B2 | 11/2008 | Reiter et al. |
| 7,476,206 B2 | 1/2009 | Palazzolo et al. |
| 7,488,293 B2 | 2/2009 | Marcovecchio et al. |
| 7,627,372 B2 | 12/2009 | Vaisnys et al. |
| 7,712,373 B2 | 5/2010 | Nagle et al. |
| 7,827,005 B2 | 11/2010 | Kimball |
| 7,831,303 B2 | 11/2010 | Rueter et al. |
| 7,913,015 B2 | 3/2011 | Kallmyer et al. |
| 7,953,478 B2 | 5/2011 | Vaisnys et al. |
| 7,974,689 B2 | 7/2011 | Volpe et al. |
| 7,991,460 B2 | 8/2011 | Fischell et al. |
| 8,005,552 B2 | 8/2011 | Covey et al. |
| 8,121,683 B2 | 2/2012 | Bucher et al. |
| 8,140,154 B2 | 3/2012 | Donnelly et al. |
| 8,224,441 B2 | 7/2012 | Vaisnys et al. |
| 8,234,128 B2 | 7/2012 | Martucci et al. |
| 8,271,082 B2 | 9/2012 | Donnelly et al. |
| 8,319,632 B1 | 11/2012 | Vaisnys et al. |
| 8,334,768 B2 | 12/2012 | Eaton et al. |
| 8,369,944 B2 | 2/2013 | Macho et al. |
| 8,406,842 B2 | 3/2013 | Kaib et al. |
| 8,475,367 B1 | 7/2013 | Yuen et al. |
| 8,494,628 B2 | 7/2013 | Vaisnys et al. |
| 8,644,925 B2 | 2/2014 | Volpe et al. |
| 8,649,861 B2 | 2/2014 | Donnelly et al. |
| 8,676,313 B2 | 3/2014 | Volpe et al. |
| 8,706,215 B2 | 4/2014 | Kaib et al. |
| 8,768,441 B2 | 7/2014 | De Zwart et al. |
| 8,774,917 B2 | 7/2014 | Macho et al. |
| 8,781,577 B2 | 7/2014 | Freeman |
| 8,880,196 B2 | 11/2014 | Kaib |
| 8,897,860 B2 | 11/2014 | Volpe et al. |
| 8,904,214 B2 | 12/2014 | Volpe et al. |
| 9,283,399 B2 | 3/2016 | Donnelly et al. |
| 10,029,108 B2 | 7/2018 | Powers et al. |
| 10,272,010 B2 | 4/2019 | Freeman et al. |
| 10,426,342 B2 | 10/2019 | Hresko et al. |
| 10,561,852 B2 | 2/2020 | Murphy et al. |
| 10,744,057 B2 | 8/2020 | Freeman et al. |
| 2001/0031991 A1 | 10/2001 | Russial |
| 2002/0052539 A1 | 5/2002 | Haller et al. |
| 2002/0181680 A1 | 12/2002 | Linder et al. |
| 2003/0004547 A1 | 1/2003 | Owen et al. |
| 2003/0032988 A1 | 2/2003 | Fincke |
| 2003/0095648 A1 | 5/2003 | Kaib et al. |
| 2003/0212311 A1 | 11/2003 | Nova et al. |
| 2004/0049233 A1 | 3/2004 | Edwards |
| 2005/0131465 A1 | 6/2005 | Freeman et al. |
| 2005/0246199 A1 | 11/2005 | Futch |
| 2005/0283198 A1 | 12/2005 | Haubrich et al. |
| 2006/0015148 A1 | 1/2006 | McCabe et al. |
| 2006/0059976 A1 | 3/2006 | Simonenko et al. |
| 2006/0095091 A1 | 5/2006 | Drew et al. |
| 2006/0136000 A1 | 6/2006 | Bowers |
| 2006/0211934 A1 | 9/2006 | Hassonjee et al. |
| 2006/0259080 A1 | 11/2006 | Vaisnys et al. |
| 2007/0129769 A1 | 6/2007 | Bourget et al. |
| 2007/0232946 A1 | 10/2007 | Feild et al. |
| 2008/0001735 A1* | 1/2008 | Tran ................. A61B 5/6806 340/539.22 |
| 2008/0033495 A1 | 2/2008 | Kumar |
| 2008/0058884 A1 | 3/2008 | Matos |
| 2008/0097793 A1 | 4/2008 | Dicks et al. |
| 2008/0103402 A1 | 5/2008 | Stickney et al. |
| 2008/0249591 A1 | 10/2008 | Gaw et al. |
| 2008/0287749 A1 | 11/2008 | Reuter |
| 2008/0306560 A1 | 12/2008 | Macho et al. |
| 2008/0306562 A1 | 12/2008 | Donnelly et al. |
| 2008/0312709 A1 | 12/2008 | Volpe et al. |
| 2009/0058635 A1 | 3/2009 | LaLonde et al. |
| 2009/0073991 A1 | 3/2009 | Landrum et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076346 A1 | 3/2009 | James et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076559 A1 | 3/2009 | Libbus et al. |
| 2009/0146822 A1 | 6/2009 | Soliman |
| 2009/0234410 A1 | 9/2009 | Libbus et al. |
| 2009/0264792 A1 | 10/2009 | Mazar |
| 2009/0292194 A1 | 11/2009 | Libbus et al. |
| 2009/0312650 A1 | 12/2009 | Maile et al. |
| 2010/0010559 A1 | 1/2010 | Zhang et al. |
| 2010/0052892 A1 | 3/2010 | Allen et al. |
| 2010/0069735 A1 | 3/2010 | Berkner |

(56) References Cited

U.S. PATENT DOCUMENTS

| | | |
|---|---|---|
| 2010/0076533 A1 | 3/2010 | Dar et al. |
| 2010/0295674 A1 | 11/2010 | Hsieh et al. |
| 2010/0298899 A1 | 11/2010 | Donnelly et al. |
| 2010/0312297 A1 | 12/2010 | Volpe et al. |
| 2011/0022105 A9 | 1/2011 | Owen et al. |
| 2011/0093840 A1 | 4/2011 | Pynenburg et al. |
| 2011/0098765 A1 | 4/2011 | Patel |
| 2011/0170692 A1 | 7/2011 | Konrad et al. |
| 2011/0172550 A1 | 7/2011 | Martin et al. |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0112903 A1 | 5/2012 | Kaib et al. |
| 2012/0146797 A1 | 6/2012 | Oskin et al. |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0266251 A1* | 10/2012 | Birtwhistle ............ H04W 12/50 726/26 |
| 2012/0277642 A1 | 11/2012 | Smith et al. |
| 2012/0283794 A1 | 11/2012 | Kaib et al. |
| 2012/0289809 A1 | 11/2012 | Kaib et al. |
| 2012/0293323 A1 | 11/2012 | Kaib et al. |
| 2012/0302860 A1 | 11/2012 | Volpe et al. |
| 2013/0013014 A1 | 1/2013 | Donnelly et al. |
| 2013/0060149 A1 | 3/2013 | Song et al. |
| 2013/0066653 A1 | 3/2013 | Joao et al. |
| 2013/0085538 A1 | 4/2013 | Volpe et al. |
| 2013/0113496 A1 | 5/2013 | Craige, III et al. |
| 2013/0144355 A1 | 6/2013 | Macho et al. |
| 2013/0218252 A1 | 8/2013 | Kaib et al. |
| 2013/0231711 A1 | 9/2013 | Kaib |
| 2013/0324868 A1 | 12/2013 | Kaib et al. |
| 2013/0325078 A1 | 12/2013 | Whiting et al. |
| 2013/0325096 A1 | 12/2013 | Dupelle et al. |
| 2014/0004814 A1 | 1/2014 | Elghazzawi |
| 2014/0031884 A1 | 1/2014 | Elghazzawi |
| 2014/0031885 A1 | 1/2014 | Elghazzawi et al. |
| 2014/0046391 A1 | 2/2014 | Cowan et al. |
| 2014/0163334 A1 | 6/2014 | Volpe et al. |
| 2014/0206974 A1 | 7/2014 | Volpe et al. |
| 2014/0249613 A1 | 9/2014 | Kaib |
| 2014/0266718 A1 | 9/2014 | Bongberg et al. |
| 2014/0277243 A1 | 9/2014 | Maskara et al. |
| 2014/0288609 A1 | 9/2014 | Freeman |
| 2014/0288610 A1 | 9/2014 | Freeman |
| 2014/0303680 A1 | 10/2014 | Donnelly et al. |
| 2014/0324112 A1 | 10/2014 | Macho et al. |
| 2014/0336514 A1 | 11/2014 | Peyman |
| 2014/0379225 A1 | 12/2014 | Nakanishi |
| 2015/0005588 A1 | 1/2015 | Herken et al. |
| 2015/0035654 A1 | 2/2015 | Kaib et al. |
| 2015/0037636 A1 | 2/2015 | Amsler et al. |
| 2015/0039039 A1 | 2/2015 | Macho et al. |
| 2015/0039042 A1 | 2/2015 | Amsler et al. |
| 2015/0039053 A1 | 2/2015 | Kaib et al. |
| 2015/0080699 A1 | 3/2015 | Kaib et al. |
| 2015/0224330 A1 | 8/2015 | Kaib et al. |
| 2015/0321022 A1 | 11/2015 | Sullivan et al. |
| 2016/0015986 A1 | 1/2016 | Seeberger et al. |
| 2016/0274162 A1 | 9/2016 | Freeman et al. |
| 2017/0065823 A1 | 3/2017 | Kaib et al. |
| 2017/0199797 A1 | 7/2017 | Hresko et al. |
| 2017/0296056 A1 | 10/2017 | Hresko et al. |
| 2019/0274913 A1 | 9/2019 | Freeman et al. |

FOREIGN PATENT DOCUMENTS

| | | |
|---|---|---|
| JP | 11149379 | 6/1999 |
| JP | 2002509472 | 3/2002 |
| JP | 2002514107 | 5/2002 |
| JP | 2004318839 | 11/2004 |
| JP | 2006091013 | 4/2006 |
| JP | 2008302225 | 12/2008 |
| JP | 2008302228 | 12/2008 |
| JP | 2009510631 | 3/2009 |
| JP | 2009521865 | 6/2009 |
| JP | 2009528909 | 8/2009 |
| JP | 2012003311 | 1/2012 |
| WO | 83/04171 | 12/1983 |
| WO | 1997022297 | 6/1997 |
| WO | 1998039061 | 9/1998 |
| WO | 2000030529 | 6/2002 |
| WO | 2004078259 | 9/2004 |
| WO | 2007019325 | 2/2007 |
| WO | 2009034506 | 3/2009 |
| WO | 2009122277 | 10/2009 |
| WO | 2011027459 | 3/2011 |
| WO | 2012006524 | 1/2012 |
| WO | 2012100219 | 7/2012 |
| WO | 2012149482 | 11/2012 |
| WO | 2013040214 | 3/2013 |
| WO | 2013130957 | 9/2013 |
| WO | 2014018057 | 1/2014 |
| WO | 2014018160 | 1/2014 |
| WO | 2014097035 | 6/2014 |
| WO | 2014099986 | 6/2014 |

OTHER PUBLICATIONS

American Journal of Respiratory and Critical Care Medicine, vol. 166, pp. 111-117 (2002), American Thoracic Society, ATS Statement: Guidelines for the Six-Minute Walk Test, available at http://ajrccm.atsjournals.org/cgi/content/ull/166/1/111.

http://web.archive.org/web/20030427001846/http:/www.lifecore.com/imageproduct.asp. Published by LifeCor, Inc., 2002, on a webpage owned by LifeCor, Inc.

Association for the Advancement of Medical Instrumentation, ANSI/AAMI DF80:2003, Medical Electrical Equipment—Part 2-4: Particular Requirements for the Safety of Cardiac Defibrillators (including Automated External Defibrillators) 2004, ISBN 1-57020-210-9; abstract; p. vi; p. 50, section 107.1.2.

ZOLL Medical Corporation, LifeVest Model WCD 3000 Operator's Manual, Pittsburgh, PA.

International Search Report and Written Opinion from PCT/US2013/028598 mailed May 9, 2013.

PCT Search Report and Written Opinion fpr PCT Application No. PCT/US2016/023057 dated Sep. 6, 2016, 14 pages.

\* cited by examiner

REMOTE ACCESS FOR AMBULATORY MEDICAL DEVICE

RELATED APPLICATIONS

This application is a continuation of U.S. patent application Ser. No. 16/548,079, entitled "REMOTE ACCESS FOR AMBULATORY MEDICAL DEVICE," filed Aug. 22, 2019, which is a continuation of U.S. patent application Ser. No. 15/475,282, entitled "REMOTE ACCESS FOR AMBULATORY MEDICAL DEVICE," filed Mar. 31, 2017 (now patented as U.S. Pat. No. 10,426,342), which claims benefit under 35 U.S.C. § 119 (e) of U.S. Provisional Application Ser. No. 62/315,789, entitled "REMOTE ACCESS FOR AMBULATORY MEDICAL DEVICE," filed Mar. 31, 2016, each of which is incorporated herein by reference in its entirety. The subject matter of each of the following applications is also incorporated herein by reference in its entirety: U.S. Provisional Patent Application Ser. No. 62/235,883, entitled "Training Modules for External Medical Device," filed Oct. 1, 2015; U.S. application Ser. No. 15/397,102, entitled "PATIENT ASSURANCE SYSTEM AND METHOD," filed Jan. 3, 2017; U.S. application Ser. No. 15/073,923, entitled "Systems and Methods for Testing a Medical Device," filed Mar. 18, 2016 (now patented as U.S. Pat. No. 10,272,010); and U.S. application Ser. No. 15/233,245, entitled "SECURE LIMITED COMPONENTS FOR USE WITH MEDICAL DEVICES," filed Aug. 10, 2016 (now patented as U.S. Pat. No. 10,252,070).

BACKGROUND

This disclosure relates generally to external medical devices, and more specifically, to techniques for remotely controlling and determining a status of an ambulatory medical device.

There are a wide variety of electronic and mechanical medical devices for monitoring and treating medical conditions, such as cardiac arrhythmias. For instance, such medical devices may continuously or substantially continuously monitor the patient for a treatable medical event via one or more sensing electrodes. When a treatable event is detected, such as a treatable cardiac arrhythmia, these medical devices may apply corrective electrical pulses or other therapeutic treatments directly to the patient through one or more therapy electrodes, or otherwise perform one or more actions triggered by the detection of the event, such as generating an alarm.

Medical devices may experience technical problems in use that impair certain functions, including functions for detecting or treating critical medical conditions. Further, medical devices may need to be updated with new information in the field. In some cases, the patient or a technical professional may need to examine the device to identify or resolve the problem. Such examination or updates may be more difficult to perform if the device malfunctions while a patient is at his or her home or place of work and lacks the tools or skills to effectively troubleshoot the problem without assistance.

SUMMARY

Ambulatory medical devices can play an important role in many treatment regimens. Given the nature of such devices, certain aspects of the treatment regimens may occur outside of the immediate supervision of medical and technical professionals. For example, ambulatory medical devices do not fully constrain movement of the patient, thus permitting the patient to carry out a normal lifestyle while the device is in use. Often these medical devices are complex instruments, having various subsystems, components, and configuration options. As such, many patients have little knowledge or understanding of the proper operation of the devices. Therefore, patients may rely on the devices to automatically notify them when a problem is detected. However, there may be cases where the patient is unable to troubleshoot the problem on his or her own, and thus requires assistance from a technical expert. If the patient is using the device at home or in another setting where the technical expert is not located, then the technical expert may wish to directly interact with the device or observe the operation of the device from a remote location.

To this end, techniques are disclosed for remotely controlling and determining a status of an ambulatory medical device. In one example, an ambulatory medical device includes a sensor configured to monitor a signal indicative of a physiological condition of a patient over an extended period of time; a controller operatively coupled to the sensor and configured to monitor the physiological signal over the extended period of time; a remote access manager operatively coupled to the controller and configured to monitor for a command from one of a remote system or remote computing device to perform a diagnostic test; to cause the controller to perform the diagnostic test in response to the command wherein the diagnostic test comprises identifying whether an operational status of the ambulatory medical device is in a critical operational status or non-critical operational status; a user interface operatively coupled to the controller and configured to display an instruction to the patient indicative of the operational status of the ambulatory medical device wherein the instruction comprises at least one of discontinuing use of the device and contacting a remote technician where the operational status is critical operational status, and continuing use of the device and contacting a remote technician where the operational status is non-critical operational status; and a data communications interface configured to transmit data representing the operational status to a remote system.

In one example, an ambulatory medical device includes a sensor configured to monitor a signal indicative of a physiological condition of a patient over an extended period of time; a controller operatively coupled to the sensor and configured to monitor the physiological signal over the extended period of time; a remote access manager operatively coupled to the controller and configured to monitor for a command to communicate with a remote system, and to establish a communication session with the remote system in response to the command for communication between the ambulatory medical device and the remote system in real time or substantially in real time.

In one example, an ambulatory medical device includes a sensor configured to acquire a signal indicative of a physiological condition of a patient; a data communications interface; and a controller operatively coupled to the sensor and to the data communications interface, the controller configured to monitor the physiological signal, to receive a command to establish a communication session with a remote system via the data communications interface, to establish the communication session in response to receiving the command, and to transmit data representing an operational status of the ambulatory medical device to the remote system via the communication session in response to receiving the command.

In one example, an ambulatory medical device includes a sensor configured to monitor a signal indicative of a physiological condition of a patient over an extended period of time; a controller operatively coupled to the sensor and configured to monitor the physiological signal over the extended period of time; a user interface; a data communications interface configured to establish a communication session with a remote computing device; a remote access manager operatively coupled to the controller and configured to monitor for a command from a remote computing device to establish the communication session between the ambulatory medical device and the remote computing device; to cause the data communications interface to initiate the communication session in response to the command from the remote computing device; to receive from the remote computing device a request for at least one of controlling a component of the ambulatory medical device and receiving an operational status of the ambulatory medical device via the communication session; to cause the user interface to display an instruction indicative of the operational status of the ambulatory medical device wherein the instruction comprises at least one of discontinuing use of the device and contacting a remote technician where the operational status is critical operational status, and continuing use of the device and contacting a remote technician where the operational status is non-critical operational status.

In one example, an ambulatory medical device including a sensor configured to acquire a signal indicative of a physiological condition of a patient; a controller operatively coupled to the sensor and configured to monitor the physiological signal, and to perform a diagnostic test; and a remote access manager operatively coupled to the controller and configured to monitor for a command from a remote system to perform the diagnostic test, and to cause the controller to perform the diagnostic test in response to the command. In the device, the remote access manager may be further configured to transmit data representing an operational status of the ambulatory medical device to the remote system. The operational status of the controller may result from performing the diagnostic test. The remote access manager may be further configured to send the data representing the operational status of the ambulatory medical device in real time or substantially in real time. The data representing the operational status of the ambulatory medical device may include a web page configured to present a virtual user interface to the ambulatory medical device via a web browser.

The device may include a security manager operatively coupled to the controller and configured to limit an ability of the remote system to control the ambulatory medical device. The device may include a device configured to administer a therapeutic treatment to a patient based on the monitored physiological signal. The device may include a base station configured to communicate with the controller, where the command from the remote system is routed to the controller via the base station. The remote system may include the base station. The remote access manager may be further configured to detect an anomalous condition of the controller, and to transmit data representing an operational status of the ambulatory medical device to the remote system in response to detecting the anomalous condition. The command from the remote system to perform the diagnostic test may include a text message received over a fixed line telecommunications network or a mobile telecommunications network. The ambulatory medical device may be configured to operate in a low power mode or a normal power mode, where the ambulatory medical device consumes less power while operating in the low power mode than while operating in the normal power mode. The remote access manager may be further configured to periodically monitor for the command less frequently while the ambulatory medical device is operating in the low power mode than while the ambulatory medical device is operating in the normal power mode.

The device may include a wearable medical device or a cardiac monitoring device. The ambulatory medical device may be configured to be operatively coupled to a garment worn about a torso of a patient.

In one example, an ambulatory medical device includes a sensor configured to acquire a signal indicative of a physiological condition of a patient; a controller operatively coupled to the sensor and configured to monitor the physiological signal, and to perform a diagnostic test; and a remote access manager operatively coupled to the controller and configured to monitor for a command to communicate with a remote system, and to establish a communication session with the remote system in response to the command. The remote access manager may be further configured to cause the controller to perform the diagnostic test in response to receiving, from the remote system and via the communication session, a command to perform the diagnostic test. The remote access manager may be further configured to transmit data representing an operational status of the ambulatory medical device to the remote system via the communication session. The data representing the operational status of the ambulatory medical device may be transmitted in response to the command. The remote access manager may be further configured to detect an anomalous condition of the controller, and to transmit the data representing the operational status of the ambulatory medical device to the remote system via the communication session in response to detecting the anomalous condition. The remote access manager may be further configured to transmit the data representing the operational status of the ambulatory medical device in real time or substantially in real time. The data representing the operational status of the ambulatory medical device may include a web page configured to present a virtual user interface to the ambulatory medical device via a web browser.

The device may include a security manager operatively coupled to the controller and configured to limit an ability of the remote system to control the ambulatory medical device. The device may include a sensor configured to detect a physiological signal. The device may include a device configured to administer a therapeutic treatment to a patient based on the monitored physiological signal. The device may include a base station configured to communicate with the controller, where the command from the remote system is routed to the controller via the base station. The controller may include the base station. The command to communicate with the remote system may include a text message received over at least one of a fixed line telecommunications network and a mobile telecommunications network. The device may include a wearable medical device or a cardiac monitoring device. The ambulatory medical device may be configured to be operatively coupled to a garment worn about a torso of a patient.

In one example, an ambulatory medical device includes a sensor configured to acquire a signal indicative of a physiological condition of a patient; a data communications interface; and a controller operatively coupled to the sensor and to the data communications interface, the controller configured to monitor the physiological signal, to receive a command to establish a communication session with a remote system via the data communications interface, to establish the communication session in response to receiving the command, and to transmit data representing an operational status of the ambulatory medical device to the remote system via the communication session in response to receiving the command. The controller may be further configured to perform a diagnostic test in response to receiving, from the remote system and via the communication session, a command to perform the diagnostic test. The operational status of the ambulatory medical device may result from performing the diagnostic test. The device may include a security manager configured to limit control of the ambulatory medical device by the remote system via the data communications interface. The ambulatory medical device may be configured to operate in a low power mode or a normal power mode, where the ambulatory medical device consumes less power while operating in the low power mode than while operating in the normal power mode. The data communications interface may be configured to be operable in the normal power mode and inoperable in the low power mode. The controller may be further configured to periodically monitor for the command less frequently while the ambulatory medical device is operating in the low power mode than while the ambulatory medical device is operating in the normal power mode.

The device may include a device configured to administer a therapeutic treatment to a patient based on the monitored physiological signal. The device may include a battery configured to provide power to the data communications interface or the controller. The device may include a base station configured to communicate with the controller, where the communication session with the remote system is routed via the data communications interface and the base station. The base station may include the controller. The controller may be further configured to detect an anomalous condition, and to transmit the data representing the operational status of the ambulatory medical device to the remote system via the communication session in response to detecting the anomalous condition. The command to establish a communication session may include a text message received over at least one of a fixed line telecommunications network and a mobile telecommunications network. The controller may be further configured to send the data representing the operational status of the ambulatory medical device in real time or substantially in real time. The data representing the operational status of the ambulatory medical device may include a web page configured to present a virtual user interface to the ambulatory medical device via a web browser. The data communications interface may be assigned a fixed Internet Protocol (IP) address. The device may include a wearable medical device or a cardiac monitoring device. The ambulatory medical device may be configured to be operatively coupled to a garment worn about a torso of a patient.

In one example, an ambulatory medical device includes a user interface disposed in the device; a data communications interface; and a controller operatively coupled to the data communications interface and the user interface, the controller configured to transmit, via the data communications interface, data representing an indication of the operational status of the ambulatory medical device to a remote system. The user interface may be configured to provide the indication of the operational status of the ambulatory medical device to a user. The indication of the operational status of the ambulatory medical device may be independent of the user interface. The user interface may include a text display, a graphics display, an input switch, a touch-sensitive screen, an indicator lamp, or an enunciator. The controller may be further configured to generate the operational status at least in part by executing a diagnostic test in response to receiving, from the remote system and via the data communications interface, a command to perform the diagnostic test. The diagnostic test may be executed without any user input via the user interface. The user interface may include a user input element configured to control an operational function of the ambulatory medical device, and the controller may be further configured perform the operational function only in response to actuation of the user input element of the user interface. The user interface may include a first user input element and a second user input element, the first user input element configured to control a first operational function of the ambulatory medical device, the second user input element configured to control a second operational function of the ambulatory medical device, and the controller may be further configured to reconfigure the user interface to cause the first user input element to control the second operational function instead of the first operational function. The controller may be configured to receive, from the remote system and via the data communications interface, a command to reconfigure the user interface. The second user input element may be in an anomalous condition. The first user input element and the second user input element may be an electrical switch, an acoustic-to-electric transducer, a photodetector, or a soft input of a touchscreen device.

The device may include a sensor configured to detect a signal indicative of a physiological condition of a patient. The device may include a device configured to administer a therapeutic treatment to a patient. The device may include a battery configured to provide power to the controller, the user interface, or the data communications interface. The device may include a sensor configured to acquire a signal indicative of a physiological condition of a patient. The controller may be configured to monitor the physiological signal.

The device may include a device configured to administer a therapeutic treatment to a patient based on the monitored physiological signal.

Still other aspects, examples and advantages of these aspects and examples, are discussed in detail below. Moreover, it is to be understood that both the foregoing information and the following detailed description are merely illustrative examples of various aspects and features, and are intended to provide an overview or framework for understanding the nature and character of the claimed aspects and examples. Any example or feature disclosed herein may be combined with any other example or feature. References to different examples are not necessarily mutually exclusive and are intended to indicate that a particular feature, structure, or characteristic described in connection with the example may be included in at least one example. The appearances of such terms herein are not necessarily all referring to the same example.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended as a definition of the limits of any particular example. The drawings, together with the remainder of the specification, serve to explain principles and operations of the described and claimed aspects and examples. In the figures, each

DETAILED DESCRIPTION

Figure 1:
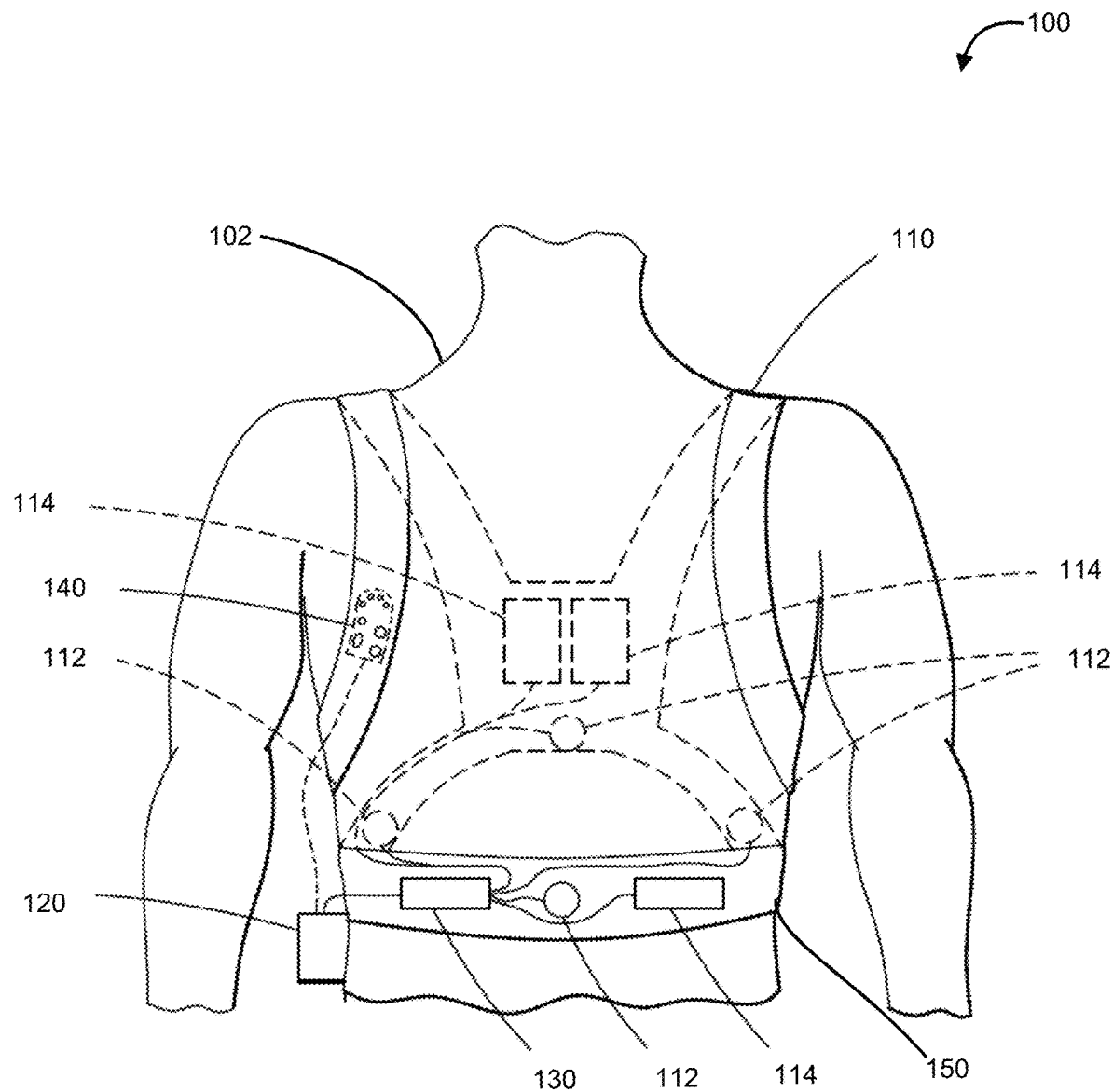
FIG. 1 illustrates an example medical device, in accordance with an example of the present disclosure.

Techniques for remotely controlling and/or determining the status of an ambulatory medical device are disclosed herein. For example, a remote person may affect the behavior of the medical device in real-time or substantially in real-time by performing one or more actions at a remote server resulting in interrogation and/or dynamic changes on the medical device. These techniques provide interested persons with the ability to remotely retrieve, from the device, information regarding the operational status of the device, as well as the ability to remotely and securely control certain functions and operations of the device. Such interested persons may include, for example, technical support personnel, medical professionals, or anyone other than the patient using the device. In some implementations, for example, a technician who is not at the patient's location may remotely and directly access the device for troubleshooting purposes during a technical assistance call with the patient. In these implementations, the technician may remotely command the device to perform one or more actions.

For instance, according to an example, a system for remotely controlling and determining a status of an ambulatory medical device includes a remote system connected, at least occasionally, to the device via a data communications network. A technician, who provides operational and troubleshooting assistance to a patient using the device, can use the system to remotely interact with the device. Such interactions may include, for example, viewing the operational status of the device, issuing commands to the device to resolve an intermittent problem with the device, resetting the device, retrieving information from the device, remotely viewing a local user interface of the device, remotely performing firmware and software updates, upgrades, or applying patches, remotely downloading and/or applying updates to underlying treatment and/or monitoring parameters, remotely changing threshold values for certain underlying treatment and/or monitoring parameters, or remotely performing other functions relating to the operation of the device. Such interactions may be performed in real-time or substantially in real-time, for example, while the patient is on the phone with the technician. In this manner, the technician can communicate directly with the patient via a telephone or Internet telephony while contemporaneously providing technical assistance via the remote system. For example, the technician may ask the patient to describe the behavior of the medical device or to press a button on the controller while speaking with the patient by telephone.

The ambulatory medical device includes a medical device controller configured to transmit data to, and receive data from, the remote system via the network. Such data may, for example, include a command to perform a diagnostic test on the device, a request to establish a communication session with the remote system, a command to reconfigure the user interface of the ambulatory medical device, data representing an operational status of the device, and other data representing control and monitoring functions of the device, such as variously described in this disclosure. The remote system can include a remote user interface and a web browser or other application configured to render at least a portion of the remote user interface.

Examples of the methods and systems discussed herein are not limited in application to the details of construction and the arrangement of components set forth in the following description or illustrated in the accompanying drawings. The methods and systems are capable of implementation in other examples and of being practiced or of being carried out in various ways. Examples of specific implementations are provided herein for illustrative purposes only and are not intended to be limiting. In particular, acts, components, elements and features discussed in connection with any one or more examples are not intended to be excluded from a similar role in any other examples.

Also, the phraseology and terminology used herein is for the purpose of description and should not be regarded as limiting. Any references to examples, components, elements or acts of the systems and methods herein referred to in the singular may also embrace examples including a plurality, and any references in plural to any example, component, element or act herein may also embrace examples including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated references is supplementary to that of this document; for irreconcilable inconsistencies, the term usage in this document controls.

Example Medical Devices

According to various examples, an ambulatory medical device is configured to enable remote retrieval of information from the device, remote control of the device, and remote diagnostic testing of the device. In some examples, this ambulatory medical device is configured to monitor a signal indicative of a physiological condition of a patient and, in some implementations, provide a therapeutic treatment to the patient based at least in part on the signal. Such remote interactions as described herein may be configured to affect changes to the manner in which the device monitors and/or provides treatment to the patient. For instance, the medical device may be configured to monitor data acquired from a patient via one or more sensors (e.g., electrocardiograph (ECG) data, heart sounds, respiration, breath sounds, tissue fluids, lung fluids, lung sounds, chest movements, and/or cardiopulmonary anomalies), detect an anomaly in the data, and provide a response to the detected anomaly. Such a response can include providing an audible or visual signal to the patient (e.g., sounding an alarm tone, illuminating a warning lamp, sounding a recorded or artificially generated voice command), displaying patient instructions, contacting a medical provider or emergency services personnel, or automatically administering a therapeutic treatment to the patient. In various implementations, the medical device is configured to monitor other patient parameters including but not limited to blood pressure, glucose levels, weight, blood oxygen, tissue fluid levels, etc. The remote interactions provided for below would allow for an authorized remote person to effect changes to the one or more aspects of the medical device as described above, including, for example, to dynamically effect changes to underlying monitoring and/or treatment parameters, effect software changes, and/or provide technical assistance.

In some examples, the ambulatory medical device is an external medical device. External medical devices as described herein may be in contrasted with internal devices, such as implantable medical devices. For example, the ambulatory medical devices as described herein may be capable of continuous, substantially continuous, long-term and/or extended monitoring of a patient or wear by, or attachment or connection to the patient. In some cases, ambulatory medical devices can be worn by, attached or otherwise connected to a patient without substantial interruption for a certain period of time. In some cases, such ambulatory medical devices can be worn by, attached or otherwise connected to a patient for several hours, several days, several weeks, or longer. For example, the ambulatory device may be configured for substantially continuous monitoring and/or treatment over various periods of time, including at least a 24 hour period, at least a week, and at least a month. For example, such medical devices can include monitoring and/or treatment devices configured to continuously monitor a patient for certain medical conditions for extended periods of time, for example, for over 4 hours (e.g. treatment and monitoring devices such as sleep apnea devices), over 12 hours (e.g. treatment and/or monitoring devices such as mobile cardiac monitoring devices, wearable defibrillator devices, etc.), and including for substantially continuous monitoring over time periods over 24 hours or even several days. Such devices may monitor the patient substantially continuously, aside from periods during which the patient may periodically remove the device, such as for showering, refitting, changing a component of the device, etc.

In some examples, the ambulatory medical device, such as disclosed herein can be used as a cardiac monitor in certain cardiac monitoring applications, such as holter monitoring, mobile cardiac telemetry (MCT) and/or continuous event monitoring (CEM) applications. The cardiac monitor may be configured to be operatively coupled to one or more physiological sensors for monitoring the patient. For example, such sensors may include ECG sensors, heart sounds sensors, RF-based fluid monitoring sensors, etc. For example, the ECG sensors may include adhesively-attached electrodes that are configured to attach to the patient's skin. In some instances, the ambulatory medical devices can carry out monitoring in periodic or aperiodic time intervals or times. For example, the monitoring during intervals or times can be triggered by a user action, a predefined monitoring condition, or another event.

The duration between the periodic or aperiodic intervals or times can be user-configurable or established by the manufacturer of the device or a qualified professional (e.g., a medical technician, pharmacist, nurse, or doctor). In some examples, the patient can interact with a user interface disposed on the cardiac monitor to identify a patient symptom. For example, such a user interface can comprise a drop down menu or check list that allows the patient to select a particular symptom from a list of alternatives. Options for patient systems can comprise one or more of: feeling a skipped beat, shortness of breath, light headedness, racing heart rate, fatigue, fainting, chest discomfort, weakness, dizziness, and/or giddiness. In addition, the patient can select a level of activity (e.g., light activity, moderate activity, rigorous activity, etc.) that he or she was performing when the symptom occurred. In some examples, in response to the selection by the patient, a cardiac event detector (e.g., cardiac event detector 426 of FIG. 4) can cause a portion of patient physiological information (e.g., in the form of a cardiac signal) to be captured for a length of time that is based on when the symptom was experienced.

In some examples, the ambulatory medical device is capable of, and designed for, moving with the patient as the patient goes about his or her normal routine. For example, the ambulatory medical device may be configured as a wearable defibrillator, such as the LifeVest® wearable defibrillator available from ZOLL® Medical Corporation of Chelmsford, Massachusetts.

FIG. 1 illustrates an example medical device 100 that is external, ambulatory, and wearable by a patient 102. The example medical device 100 is configured to enable a technician or other user to remotely monitor the device, control the device, and/or perform diagnostic tests on the device. The medical device 100 can include one or more of the following: a garment 110, one or more sensing electrodes 112 (e.g., ECG electrodes), one or more therapy electrodes 114, a monitor or a medical device controller 120, a connection pod 130, a patient interface pod 140, a belt 150, or any combination of these. In some examples, at least some of the components of the wearable medical device 100 are configured to be affixed to the garment 110 (or in some embodiments, permanently integrated into the garment 110), which can be worn about the patient's torso. The controller 120 can be operatively coupled to the sensing electrodes 112, which may be affixed to the garment 110, e.g., assembled into the garment 110. In some implementations, the sensing electrodes 112 may be permanently integrated into the garment 110. The controller 120 is operatively coupled to the therapy electrodes 114. For example, the therapy electrodes 114 may also be assembled into the garment 110, or, in some implementations, the therapy electrodes 114 may be permanently integrated into the garment 110.

Component configurations other than those shown in FIG. 1 are possible. For example, the sensing electrodes 112 are configured to be attached at various positions about the body of the patient 102. The sensing electrodes 112 can be operatively coupled to the medical device controller 120 through the connection pod 130. In some implementations, the sensing electrodes 112, the therapy electrodes 114, or both, may be adhesively attached to the patient. In an implementation, the sensing electrodes 112 and therapy electrodes 114 may be included on a single integrated patch and adhesively applied to the patient's body.

The sensing electrodes 112 are configured to detect one or more cardiac signals. Examples of such signals include ECG signals, heart sounds, and/or other sensed cardiac physiological signals from the patient. The connection pod 130 can, in some examples, include a signal processor configured to amplify, filter, and digitize these cardiac signals prior to transmitting the cardiac signals to the controller 120. One or more therapy electrodes 114 are configured to deliver one or more therapeutic defibrillating shocks to the body of the patient when the medical device 100 determines that such treatment is warranted based on the signals detected by the sensing electrodes 112 and processed by the controller 120.

One or more remote interactions may be configured to effect changes to thresholds for discriminating ECG signals in noisy environments. For instance, if a patient is encountering frequent false positives, the remote technician may be able to change device noise discrimination thresholds by establishing a remote secure communication session with the device. In some implementations, a machine learning based system may be implemented to determine whether an abnormal heart rhythm is ventricular tachycardia (VT) or ventricular fibrillation (VF). Accordingly, a method for distinguishing a cardiac event from noise in an ECG signal includes obtaining an indicating from a digital signal processing module that a cardiac event has occurred, obtained the ECG signal corresponding to the cardiac event from a memory, determining a feature of the ECG signal (e.g., a power spectral density or PSD) of the ECG signal and determining an ECG-derived score based on the PSD and corresponding to the ECG signal. A predetermined threshold can be automatically derived based on the machine learning system and used to compare against the ECG-derived score. Such a threshold may be remotely configurable via the secure remote communication session. Further details regarding noise discrimination are described in U.S. Publication No. 20160000349 (the '349 publication), entitled "SYSTEM AND METHOD FOR DISTINGUISHING A CARDIAC EVENT FROM NOISE IN AN ELECTROCARDIOGRAM (ECG) SIGNAL" and filed on Jul. 6, 2015, which is hereby incorporated herein by reference in its entirety.

Example Medical Device Controller

Figure 2A:
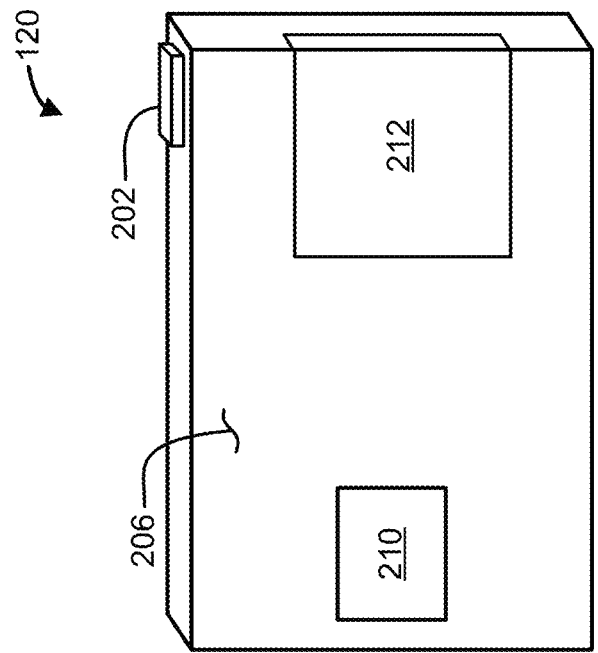
FIGS. 2A and 2B illustrate an example of a medical device controller, in accordance with an example of the present disclosure.
Figure 2B:
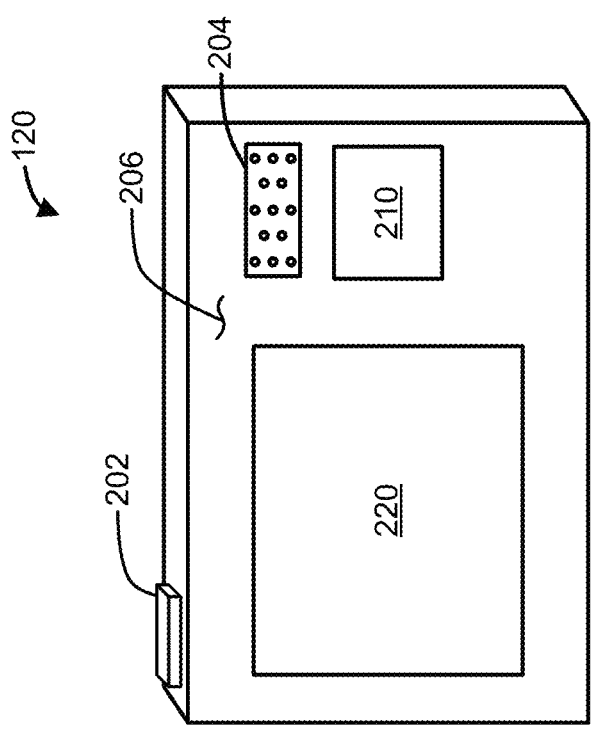

FIGS. 2A and 2B illustrate an example of the controller 120 of FIG. 1, in accordance with an example of the present disclosure. The controller 120 includes a port 202, a speaker 204, one or more user interface elements, such as a response button 210 and a display 220, a housing 206, and a battery 212 or other power source. The port 202 is configured to removably connect sensing devices (e.g., sensing electrodes 112) and/or therapeutic devices (e.g., therapy electrodes 114) to the controller 120. The speaker 204 is configured to communicate information to the patient, a caregiver, or other bystander, including audible alarms and alerts. The controller 120 and/or the patient interface pod 140 can include one or more response buttons 210, which the patient can press to respond to the device. The user interface elements can additionally or alternatively be configured to provide device status information, diagnostic information about the device, instructions, and other related information to the patient, caregiver, or bystander. In some implementations, the user input elements may, for example, include an electrical switch, an acoustic-to-electric transducer, a photodetector, a soft or virtual input of a touchscreen device, or any combination of these. The patient or caregiver can interact with the touch screen 220 or, as described below, the patient interface pod 140, to control the medical device 100. As shown in FIG. 1, the wearable medical device 100 can, in some examples, include the patient interface pod 140, which can be coupled to the medical device controller 120. In one example, the patient interface pod 140 can be electrically coupled by a cable to the controller 120. In another example, the pod 140 can be wirelessly coupled (e.g., via Bluetooth) to the controller 120. The patient interface pod 140 can, in some examples, include patient interface elements, such as a speaker, a microphone responsive to patient voice input, a display, an interactive touch screen responsive to patient touch input, physical buttons, or any combination of these. In addition to, or instead of, the touch screen 220 of the controller 120, the controller 120 may interact with the patient (e.g., receive patient input or provide information to the patient as described herein) via patient interface pod 140 (shown in FIG. 1). The patient interface pod 140 may take other forms and include additional functionality. For instance, the patient interface pod 140 may be implemented on a smartphone, tablet, or other mobile device carried by the patient. In another example, the patient interface pod 140 may be worn as a watch about the wrist of the patient, or as a band about an upper arm of the patient.

Figure 3:
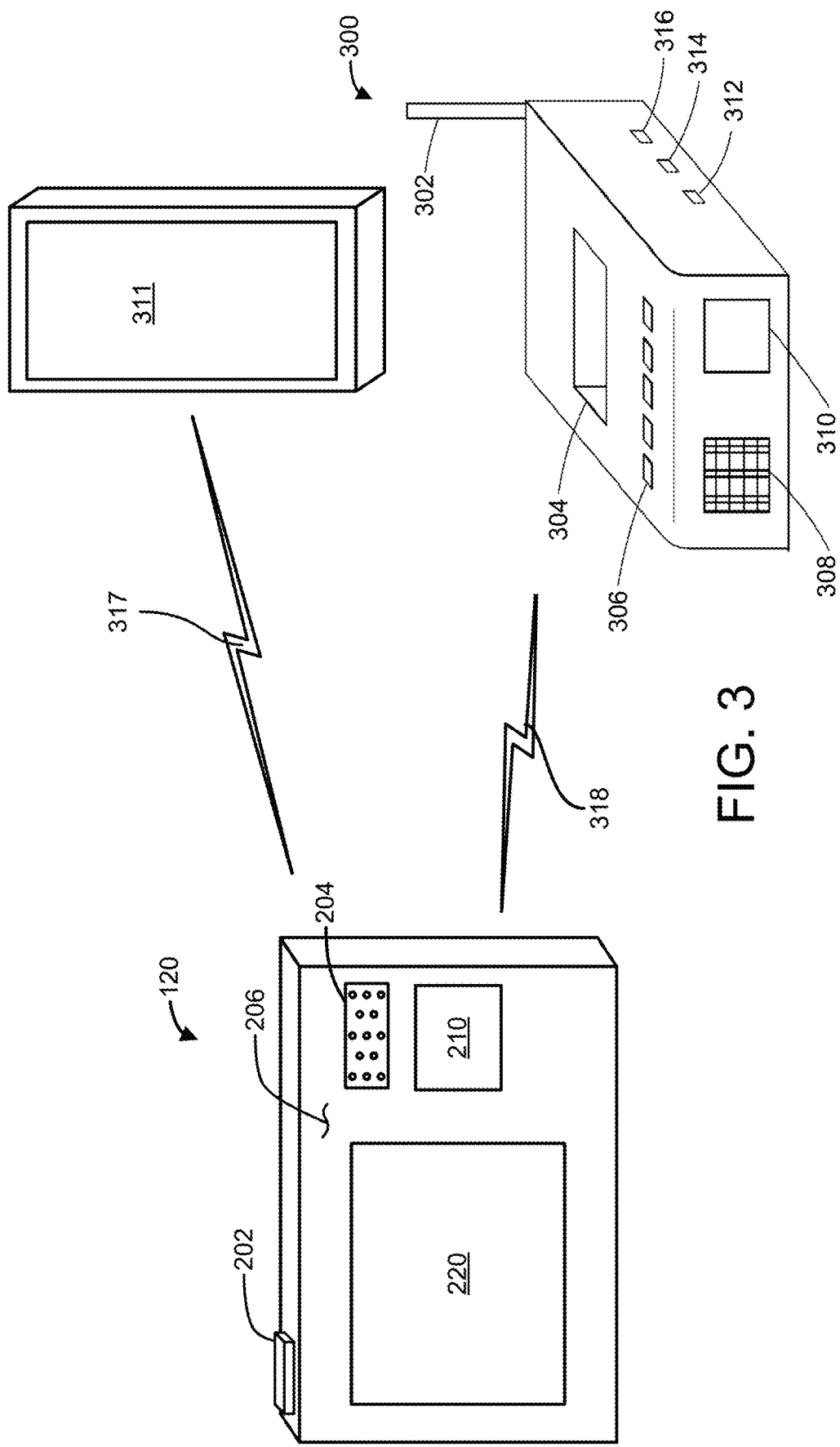
FIG. 3 illustrates the controller of FIGS. 2A and 2B, and an example base station, in accordance with an example of the present disclosure.

FIG. 3 illustrates the controller 120 of FIGS. 2A and 2B, and an example base station 300, in accordance with an example of the present disclosure. In some examples, the controller 120 is configured to communicate with the base station 300. The base station 300 includes an antenna 302, a battery charging bay 304, one or more buttons 306, a speaker 308, a display 310, and one or more communication interfaces 312, 314, and 316. The base station 300 can communicate with the controller 120 via, for example, wireless communication connection 318, e.g., BLUETOOTH, Wireless USB, ZigBee, and Wireless Ethernet. The information received by the base station 300 may be communicated over a wired or wireless communication network shortly after it is received by the base station 300, or alternatively, may be stored in a memory of the base station 300 and communicated over the network at a later time. For example, such information may be part of a remote communication session established by a remote person to establish real time or substantially real-time interaction with the device. In some examples, the base station 300 is capable of charging the removable battery 212 for the controller 120.

In some examples, the controller 120 may alternatively or in addition be in communication 317 with a mobile remote computing device 311 (e.g., a mobile phone, smart phone, tablet, or other personal device). As described in further detail below, a remote communication session 317 can be established between the controller 120 and the mobile remote computing device 311. A remote technician may perform diagnostics on the medical device controller 120 via the mobile remote computing device 317. For example, the technician may cause a remote server to send one or more instructions (e.g., in the form on action scripts) to the mobile remote computing device 317. The mobile remote computing device 317 may then be configured to control the controller 120 in a manner prescribed by the remote technician in accordance with the instructions. The mobile remote computing device 317 can communicate with the controller 120 via, for example, wireless communication connection 318, e.g., BLUETOOTH, Wireless USB, Zig-Bee, and Wireless Ethernet. The information received by the mobile remote computing device 317 from the controller 120 may be communicated over a wired or wireless communication network shortly after it is received by the mobile remote computing device 317, or alternatively, may be stored in a memory of the mobile remote computing device 317 and communicated over the network at a later time. For example, such information may be part of a remote communication session established by a remote person to establish real time or substantially real-time interaction with the device.

Figure 4:
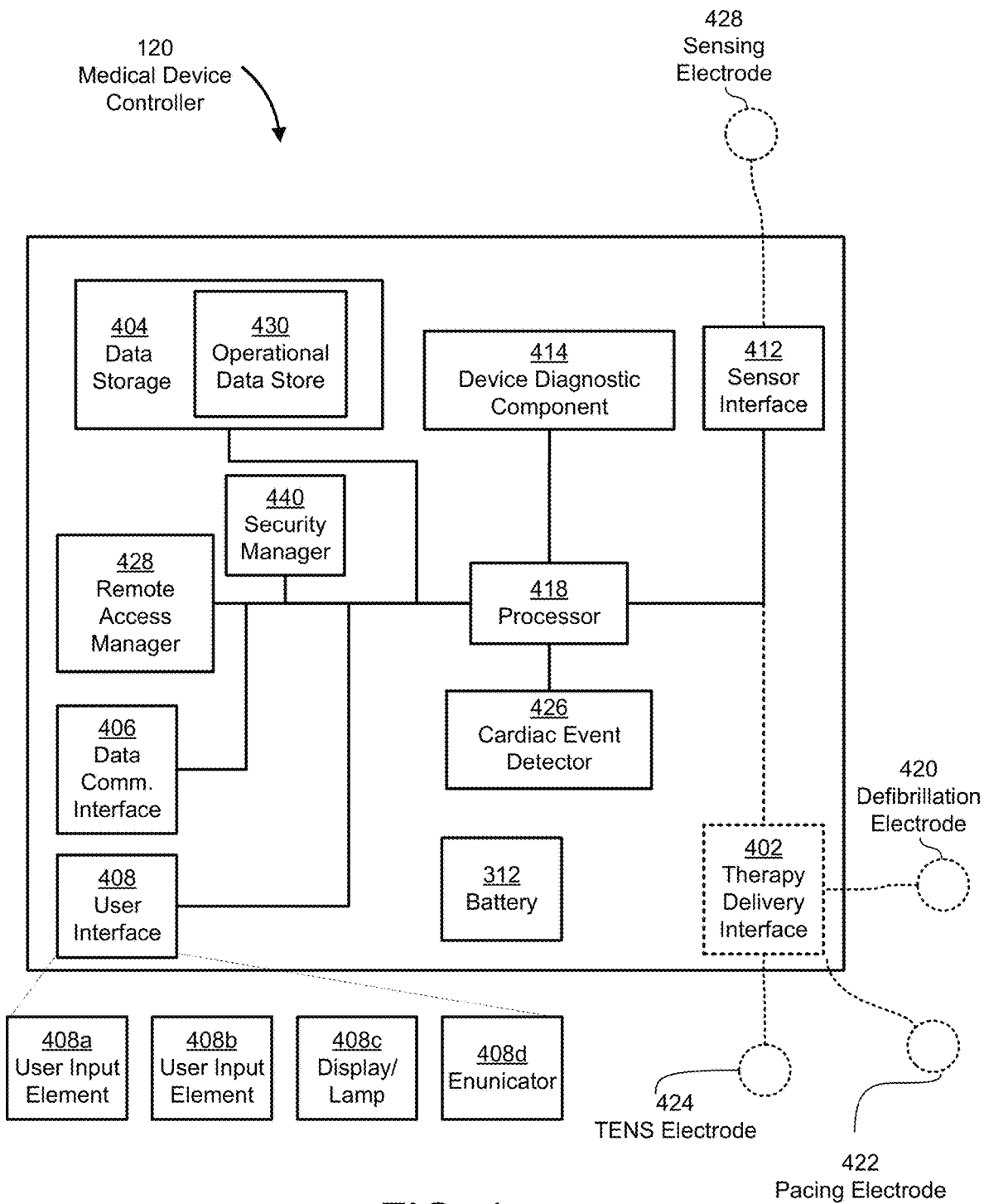
FIG. 4 shows a schematic of an example of the medical device controller of FIGS. 1, 2A, 2B, and 3, in accordance with an example of the present disclosure.

FIG. 4 shows a schematic of an example of the medical device controller 120 of FIGS. 1, 2A, 2B, and 3. In some examples, the medical device controller 120 may be adapted as a cardiac monitor as described above. The controller 120 includes a sensor interface 412, at least one processor 418, a device diagnostic component 414, an optional therapy delivery interface 402, data storage 404 (which may include operational data store 430), a data communications interface 406, a user interface 408, a remote access manager 428, a security manager 440, and the battery 312.

In some implementations, the controller 120 includes one or more computer processors 418 that are each configured to execute a series of instructions that result in manipulated data and/or control the operation of the other components of the controller 120. In some implementations, the processor 418 can be configured to include the remote access manager 428 or control the actions of the remote access manager 428 described in further detail below. In some implementations, when executing a process such as provided herein (e.g., FIGS. 9 and 13), the processor 418 is configured to make specific logic-based determinations based on input data received, and further capable of providing one or more outputs that can be used to control or otherwise inform subsequent processing to be carried out by the processor 418 and/or other processors or circuitry with which processor 418 is communicatively coupled. Thus, the processor 418 reacts to specific input stimulus in a specific way and generates a corresponding output based on that input stimulus. In this sense, the structure of processor 418 according to one example is defined by the flow chart shown in FIG. 9. In some example cases, the processor 418 proceeds through a sequence of logical transitions in which various internal register states and/or other bit cell states internal or external to the processor 418 may be set to logic high or logic low. This specific sequence of logic transitions is determined by the state of electrical input signals to the processor 418 and a special-purpose structure is effectively assumed by the processor 418 when executing each software instruction of the software process shown in, for example, FIGS. 9 and 13. Specifically, those instructions anticipate the various stimuli to be received and change the implicated memory states accordingly. In this way, the processor 418 may generate and store or otherwise provide output signals. It is appreciated that the processor 418, during execution of a process, is capable of processing specific input signals and rendering specific output signals based on the one or more logic operations performed during execution of each software instruction. As referred to herein, the processor 418 is configured to execute a function where software is stored in a data store coupled to the processor 418 that is configured to cause the processor 418 to proceed through a sequence of various logic decisions that result in the function being executed.

In some examples, the controller 120 includes an embedded operating system and features that provide relational database functionality, touch screen display drivers, audio generation, BLUETOOTH wireless networking, networking security and firewalling, a lightweight web server and data encryption services.

In some examples, the controller 120 is configured to receive a request to establish a communication session with a remote system via the data communications interface 406, and to establish the communication session in response to receiving the request without any interaction by the patient. In some implementations, the patient may be prompted to authorize the initiation of the session. For instance, the patient may be prompted to enter a passphase or provide other such form of authorization. For example, if a remote technician wishes to establish a communication session with the medical device 100 for troubleshooting purposes, the technician may cause the remote system to send a communications session request to the device 100. The device, in turn, may receive the request substantially immediately after the request is sent, or at some future point in time, and open the communication session automatically. After the communication session has been established in response to receiving the request, the controller may transmit data representing an operational status of the ambulatory medical device to the remote system via the communication session.

The sensor interface 412 can be coupled to any one or combination of sensors to receive a signal indicative a physiological condition of the patient. For example, the sensor interface 412 may be coupled to one or more sensing devices including sensing electrodes 428 (e.g., sensing electrodes 112 of FIG. 1). The therapy delivery interface 402 (if included) can be coupled to one or more electrodes that provide therapy to the patient including, for example, one or more defibrillation electrodes 420, pacing electrodes 422, and/or TENS electrodes 424. In some examples, the controller 120 includes a cardiac event detector 426 to monitor the cardiac activity of the patient and identify cardiac events experienced by the patient based on the physiological signal. In response to identifying certain cardiac events, the controller 120 is configured to administer a therapeutic treatment to the patient via the therapy delivery interface 402, such as described above.

In some examples, the data communications interface 406 is configured to facilitate the communication of data and information over a data communications network between the controller 120 and one or more other devices or entities (e.g., a remote system or a technician providing remote assistance to the patient). In some examples, the data communications interface 406 is configured to communicate with a remote system (e.g., a computer server that may be accessed via a telephony network, a wide area network, or the Internet) or other electronic device, where a technician can access information related to the medical device 100 or with a base station (e.g., the base station 200) that is associated (e.g., paired) with the controller 120. According to an example, the data communications interface 406 is configured to provide a data pathway between the remote system and certain components of the controller 120, including the remote access manager 428. This pathway can directly link the controller 120 to the remote system, or the pathway can be routed from the controller 120 to the remote system via the base station 300. In some examples, at least a portion of the pathway includes a BLUETOOTH or other wireless connection between the controller 120 and the base station 300.

Figure 6:
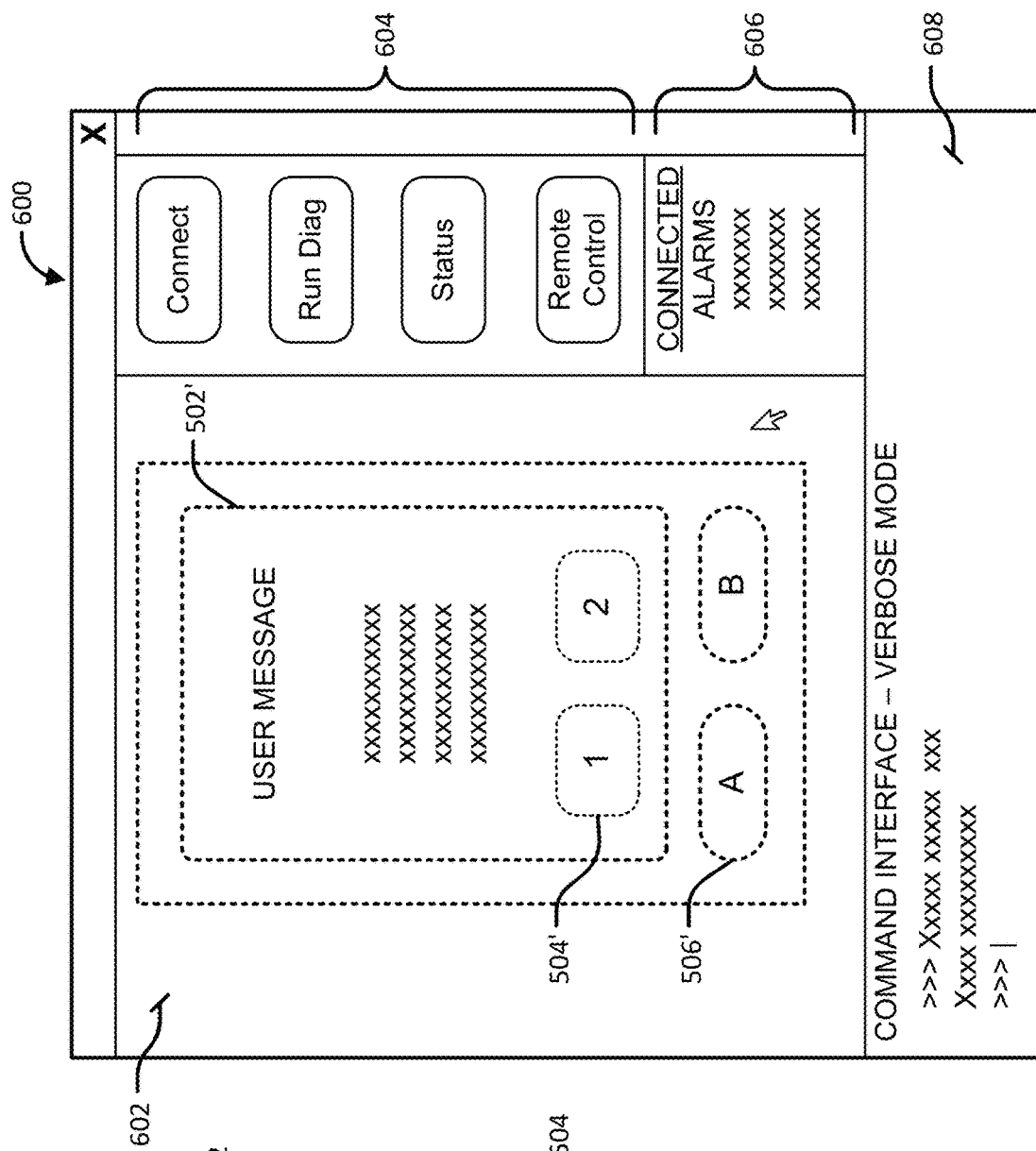
FIG. 6 shows another example user interface, in accordance with an example of the present disclosure.

In some examples, the user interface 408 includes one or more physical interface elements such as user input elements 408a, 408b, displays, lamps and indicators 408c, enunciators and audio speakers 408d, and other input devices, output devices, and combination input/output devices. These user interface elements may render visual, audio, and/or tactile content, including content relating to the device health status. For instance, in some examples, the user interface 408 includes a microphone, the speaker 204, the display 220, and the response buttons 210, as shown in FIGS. 2A and 2B. In some examples, the user interface 408 includes one or more electrical switches, one or more acoustic-to-electrical transducers, one or more photodetectors, and one or more soft or virtual user input elements associated with a touch-sensitive screen device. Thus the user interface 408 may receive input or provide output, thereby enabling a user to interface with the controller 120. FIG. 6 shows another example user interface 408, which is described in further detail below.

Example Remote Access Manager

According to some examples, the remote access manager 428 is configured to monitor for a command from a remote system to perform a diagnostic test on the ambulatory medical device 100 and to cause the controller 120 to perform the diagnostic test in response to the command. For instance, in one example, the remote access manager 428 is configured to receive commands for the controller 120 from the remote system via the data communications interface 406. In examples, the remote system may be a remote server administered by a monitoring service, a health care organization, or other entity. For example, the remote system may be implemented as a local area network, a private network, a virtual private network, or server-based networked computer system containing one or more networked devices (e.g., a computer, smartphone, tablet or other workstation).

According to some examples, the remote access manager 428 is configured to monitor for a request to communicate with a remote system and to establish a communication session with the remote system in response to the request. For instance, in one example, the remote access manager 428 is configured to send data from the controller 120 to the remote system via the data communications interface 406.

In some examples, commands received by the controller 120 or the remote access manager 428, data generated by the device 100, or other information related to the device 100 may be temporarily stored in a memory device of the base station 300 (e.g., via BLUETOOTH, WiFi, or other wireless communication channel). For example, the base station 300 may temporarily store commands, messages, and other information while the controller 120 is not within wireless communication range of the base station 300. In one example, such commands, messages, and other information may be stored in the form of action files in a memory of the base station 300. An action file may specify a sequence of instructions configured to be automatically executed by the controller 120. Similarly, the controller 120 may connect to the base station 300 and upload information collected by the device during its operation.

For instance, information that is uploaded from or downloaded to the ambulatory medical device via a communication session may vary depending on the type of medical device. For example, a cardiac monitor may exchange information relating to cardiac monitoring thresholds as described below. For example, a defibrillator may exchange information relating to treatment thresholds, such as shock energy levels, number of pulses, duration of pulses, etc. In general, such information can include patient information, device status information, and other operational data. Patient information in this context may include ECG information, such as atrial fibrillation (AF), changes in QRS (e.g.: width, height, or other such parameter), change in (s-t) t-wave, ventricular tachycardia (VT), ventricular fibrillation (VF), tachycardia (e.g., above a specified threshold), bradycardia (e.g., heart rate falling below a specified threshold, significant pauses (e.g., triggered by a predetermined threshold), and pre-ventricular contractions (PVCs). For example, when a PVC count threshold is exceeded, the patient information may be uploaded to an analyst for further review by activating a user interface element on the device. Patient information may include patient reported symptom information, for example, when the patient reports (e.g., by activation of a user interface element) dizziness, palpitations, chest pain, etc. Patient information may include a non-treatable rhythm, e.g., a rhythm detected by the device but not treatable by the device. For example, a normal ECG may be affected by noise, which causes the data to be flagged for further review by an analyst. In some examples, the ECG may include PVCs, which may also cause the data to be flagged for further review by an analyst. In such cases, the analyst may use the remote communication session to review the patient's ECG and establish the nature of the issue flagged by the device. The analyst may then cause an ECG template (e.g., a template having a form of PVC matter that the analyst selects based on his or her review) to be downloaded to the device via the remote communication session. The device may use the template to filter out or disregard certain noise or PVC patterns. In cases where the analyst re-characterizes the template, the generated template can be downloaded to the device and activated dynamically via the remote communication session without patient intervention. Other patient information that may be affected in a similar manner includes change in patient fluid levels, respiration information, accelerometer-detected patient falls, walk test activation and data, cardiac sounds or measures such as an S3, S4, or prolonged electromechanical activation times (EMAT). The data may be configured to be exchanged on a continuous, periodic, or aperiodic basis.

After the controller 120 enters the wireless communication range of the base station 300, a wireless connection can be established and the information stored on the base station 300 can be transmitted to the controller 120. Similarly, information can be temporarily stored on the base station 300 while no data connection is present between the base station 300 and the remote system. After the base station 300 establishes such a data connection, the information stored on the base station 300 can be transmitted to the remote system. In this sense, some data communications between the controller 120 and the remote system are asynchronous (i.e., not contemporaneous), but instead are buffered on the base station 300 until the corresponding data communications connections are established and the information transfer can be completed.

In some cases, a doctor or an external monitoring service may activate the remote communication session to request patient data, as described above, or device data. For example, the server receiving such information may be configured to perform analysis on the returned data, including study trends, and provide one or more reporting functions to predetermined end-users and/or devices. For example, reports can be generated in specified intervals (e.g., weekly, daily, or hourly). Reports may also be generated based on onset of certain events (e.g., cardiac events described above).

The doctor or external monitoring service may use the remote communication session to cause instructions to be sent to the patient. In some examples, the doctor or external monitoring service may also remotely cause the device changes to the patient's monitoring parameters, treatment regimen, or other device configurations. As an illustration, a patient wearing a cardiac monitor or a defibrillator may be sent a set of customized instructions (e.g., personalized to the particular patient) to perform a walk test. Such instructions may include reminders to take medication prior to performing the activity, how to perform the activity, pace and speed information, among others, and may be delivered in a preferred language of the patient. In addition, a doctor may indicate that one or more physiological parameters of the patient, e.g., heart rate, ECG, and respiration sounds, is to be monitored during the performance of the test. For example, the device may permit a doctor or other healthcare provider to remotely monitor one or more of the physiological parameters of the patient in real time or near real time while the patient is performing a physical activity while wearing the device, such as a walk test. The monitoring may be activated manually by the patient using the user interface of the device, or remotely activated by sending a command to the device. If the monitoring is remotely activated, the patient may be asked to acknowledge the monitoring by activating a user interface element (e.g., press a button or touch the screen) before the remote monitoring begins, or the patient may be notified of the monitoring by displaying a message on the user interface and/or sounding an audible cue. During the monitoring, the device may upload data representing the monitored parameters to the remote server as the data is collected. The doctor may also indicate that if certain thresholds are transgressed (e.g., heart rate exceeds 130 beats per minute), then the patient may be instructed to pause, suspend, or stop the activity.

In another illustration, a patient wearing a cardiac monitor or a defibrillator may call technical support to report a problem with electrode noise and false alerts. The technician may use a report communication session as described herein to access the patient's device. In real-time or substantially real-time, the technician may instruct the patient to adjust his or her electrodes and view the changes in signals as the patient is following the instructions.

In some examples, the remote access manager 428 is configured to receive from a remote system a request to configure or re-configure the medical device in real time or in substantially real-time. A technician or other authorized entity send one or more commands, messages, or other instructions to the remote access manager 428 to cause the medical device to initiate or re-initiate the device with data pertaining to the patient associated or to be associated with the device. For example, cardiac devices such as cardiac monitors and defibrillators may be remotely configured with certain initial information. Such information may include patient-specific information, e.g. the patient's name, date of birth, a unique identifier, a start date for device use, an estimated length of use of the device, and one or more reasons for the device being prescribed to the patient (e.g., cardiac arrest due to VT/VF, familial or inherited health condition with sudden cardiac arrest risk, myocardial infarction (MI) with an ejection fraction (EF) of less than a predetermined value, say, 35%, Ischemic Cardiomyopathy (NICM), or other Dilated Cardiomyopathy (DCM) with EF<35%, among others). In some implementations, the remotely provided configuration information can also include threshold values for one or more parameters. For a defibrillator or other cardiac therapeutic device certain threshold values may be provided: a VT threshold value (e.g., 150 bpm), a VF threshold value (e.g., 200 bpm), and values for one or more treatment pulses (e.g., 75 Joules for a first pulse, 100 joules for a second pulse, 125 joules for a third pulse, and so on). The patient-specific and/or device configuration information can be remotely reconfigured over the communication session. As such, if any of the information, e.g., patient's details, dates and/or length of use, or other device configuration information such as VT threshold value, VF threshold value, and/or treatment pulse energy levels needs to be changed, a technician or reviewer can use the remote communication session to effect the change on the medical device.

Example Security Manager

According to an example, the security manager 440 is configured to limit an ability of the remote system to control or obtain information from the ambulatory medical device 100. For example, the security manager 440 may be configured to prevent the remote system from altering or otherwise affecting any critical device functions, such as treatment parameters, critical device self-tests, and power management. For instance, the security manager 440 may be configured to intercept, and prevent the device from executing, certain commands that could power down the device or put the device into a mode that prevents the device from administering a treatment to the patient, detecting a physiological signal of the patient, or disabling any alarms. In another example, the security manager 440 may be configured to prevent private information (e.g., certain data relating to the physiological signal of the patient, certain patient health information, or the identity or location of the patient) from being transmitted to the remote system. In some examples, the security manager 440 can intercept certain commands and other data from the remote access manager 428 before such commands and data reach or affect other components of the device (e.g., the cardiac event detector 426, the device diagnostic component 414, the sensor interface 412, and the therapy delivery interface 402), effectively acting as a firewall between those components and the remote access manager 428. In some examples, some or all aspects of the security manager 440 can be integrated with the remote access manager 428 or the data communications interface 406.

Example Device Diagnostic Component

According to an example, the device diagnostic component 414 is configured to receive a request to perform a diagnostic test on the ambulatory medical device 100, to query data sources within the controller 120 for operational status information, to perform normal operations and collect the results of such operations, to report or transmit the operational status information or results, or any combination of these. The device diagnostic component 414 may, for example, be configured to execute one or more tests that evaluate the operational integrity or state of various components, circuits, and/or subsystems of the ambulatory medical device 100, including, for example, the controller 120. In some cases, the device diagnostic component 414 is configured to receive, from the remote system via the remote access manager 428, a command to execute a test. In response to receiving such a command, the device diagnostic component 414 may execute one or more tests designed to reveal whether or not the device is operating as intended by the manufacturer. For example, the tests may be designed to evaluate whether certain components of the device 120, such as processor 418, the data communications interface 406, the cardiac event detector 426, the sensor interface 412, and the therapy delivery interface 402 are functioning normally or abnormally, or to otherwise generate information describing the condition of the device. In some examples, the device diagnostic component 414 is configured to transmit data representing the results of the tests, or data representing various operating states or conditions of the device 100, to the remote system, either in response to a request or command from the remote system or in response to another event, such as a change in state or operational conditions (e.g., the activation of a function by the patient via the user interface 408 or the activation of a function by the cardiac event detector 428). Other examples of the device diagnostic component 414 are described in U.S. patent application Ser. No. 15/397,102, entitled "PATIENT ASSURANCE SYSTEM AND METHOD" and filed on Jan. 3, 2017, which is incorporated herein by reference in its entirety.

In some examples, to identify the one or more data sources to query with respect to remotely determining updated diagnostic information, the remote access manager 428 is configured to access one or more data structures that identify data sources. These data structures may be stored in the operational data store 430, along with previously generated device operational status information and results of diagnostic tests. In some examples, the one or more data structures that identify the data sources combine to form a table in memory storage (e.g., operational data store 430) that associates the data sources with one or more subsystems of the ambulatory medical device 100.

For example, the operational data store 430 may store identifiers of data sources in association with identifiers of the subsystems. The operational data store 430 can be configured to associate multiple data sources (e.g., one for each test executable by the device diagnostic component 414) with subsystems of a medical device. More specifically, the store 430 can be configured to associate data sources with a monitor subsystem, an electrode subsystem, a battery subsystem, a base station subsystem, a garment subsystem, and a communications subsystem. The components included in each of the subsystems may vary between examples. However, the monitor subsystem generally includes the controller 120 and its components, as illustrated in FIGS. 1, 2A, 2B, 3, and 4. In some examples, the monitor subsystem includes a processing subsystem that includes the processor 418 and the data storage 404. The electrode subsystem generally includes the therapy electrodes 114, the sensing electrodes 112, the connection pod 130, and associated wires and cables, as illustrated in FIG. 1. The battery subsystem generally includes the battery 212, as illustrated in FIGS. 2A and 2B. The base station subsystem generally includes the base station 300 and its components, as illustrated in FIG. 3. In some examples, the base station subsystem includes a battery charger subsystem that includes a battery charging circuit. The garment subsystem generally includes the garment 110 and its components, as illustrated in FIG. 1. In some examples, the electrode subsystem includes a gel deployment subsystem, sensing electrode subsystem, a therapy electrode subsystem, and a signal acquisition and processing subsystem, which includes the connection pod 130. In at least one of these examples, the gel deployment subsystem is configured to dispense impedance reducing gel on the patient's body. In some examples, the monitor subsystem, the electrode subsystem, the garment subsystem, and the battery subsystem include an energy storage and delivery subsystem that includes the battery 212, the therapy delivery interface 402, and the therapy electrodes 114. The communications subsystem generally includes the network interface 406 and/or communication components housed in the base station 300.

In some examples, one or more remotely triggered device diagnostic tests associated with the monitor subsystem includes tests that validate the operational integrity of processing elements (e.g., the processor 418), memory elements (e.g., the data storage 404), user interface elements (e.g., the user interface 408), and therapy deliver elements (e.g., the therapy delivery interface 402). For instance, one or more remotely triggered diagnostic tests associated with the monitor subsystem may check the capacitor charging circuit to verify the capacitors can be charged appropriately for delivery of one or more therapeutic defibrillating and/or pacing pulses.

In some examples, the one or more remotely triggered diagnostic tests associated with the electrode subsystem include tests that validate the operational integrity of sensing electrodes (e.g., the sensing electrodes 112), therapy electrodes (e.g., the therapy electrodes 114), the gel deployment subsystem, and/or a vibration box (e.g., part of the user interface 408) located in a connection pod (e.g., the connection pod 130). For instance, the one or more remotely triggered diagnostic tests associated with the electrode subsystem may check to ensure that the electrode cables have not experienced tensile forces in excess of a threshold value and that the signal strength and impedance measured at the electrodes in the electrode subsystem are within one or more acceptable ranges.

For example, a combination of software and hardware tests may include mechanisms that simulate an input and read one or more resulting outputs. The outputs may then be compared to a set of known good values and it is then determined if a component within the one or more subsystems (e.g., the electrode subsystem) is malfunctioning or requires calibration. For example, critical components on the electrode subsystem may include accelerometer, gyro, heart sounds sensor, and analog front end for receiving ECG and/or electrical signals from the patient. The software and/or hardware test circuitry may include signal generators for generating test stimulus signals. Additional diagnostic tests are described in in U.S. application Ser. No. 15/073,923, entitled "SYSTEMS AND METHODS FOR TESTING A MEDICAL DEVICE" and filed on Mar. 18, 2016, which is incorporated herein by reference in its entirety.

Example Local-Remote User Interfaces

Figure 5:
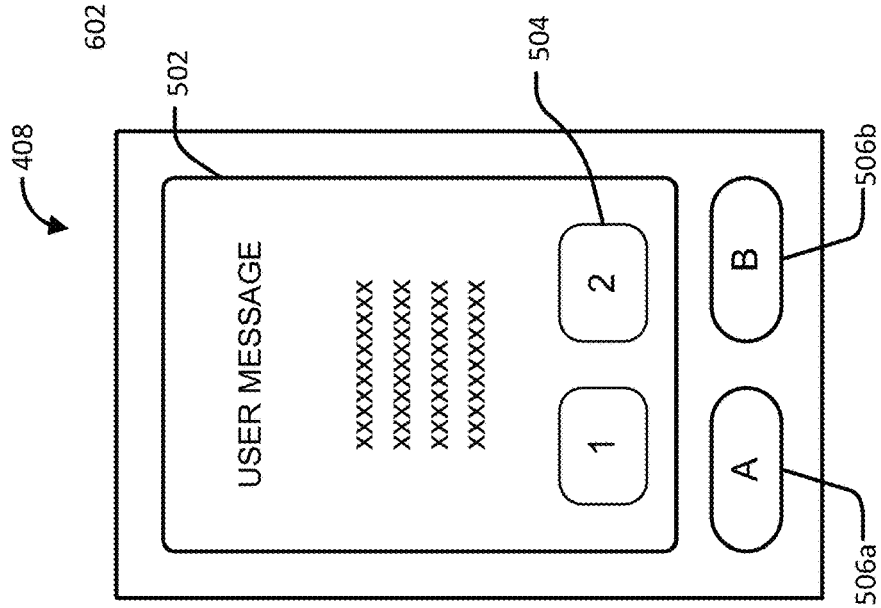
FIG. 5 shows an example user interface, in accordance with an example of the present disclosure.

FIG. 5 shows an example user interface 408 that can be implemented into the ambulatory controller 120, in accordance with an example. In this example, the user interface 408 includes a display screen 502 configured to display text and graphics generated at least in part by the controller 120. The display screen 502 can, in some examples, be a touch-sensitive display screen that is configured to detect a physical contact by a finger or other object. In such cases, the screen 502 may be configured to display one or more virtual user input elements 504 that are programmed to behave in the same manner as a physical user input element, such as a button or switch. The user interface 408 can include, in some examples, one or more of such physical user input elements 506a and 506b, in addition to or instead of the virtual user input elements 504.

In some cases, the user interface 408 is configured to provide an indication of the operational status of the ambulatory medical device to a user. In some such cases, the indication of the operational status of the ambulatory medical device is independent of the user interface 408 (e.g., the indication of the operational status may not be displayed to the patient in the user interface due to a configuration setting preventing such display or due to a failure of the user interface to display the operational status). In this manner, the remote system can obtain the operational status of the medical device even if the local user interface is not contemporaneously displaying the status to the patient.

In some cases, the controller 120 is configured to generate the operational status at least in part by executing a diagnostic test in response to receiving, from the remote system and via the data communications interface, a command to perform the diagnostic test. In some such cases, the diagnostic test is executed without any user input via the user interface 408.

In some cases, the user interface 408 includes one or more user input elements, such as physical buttons 506a, 506b or virtual buttons 504 on a touch screen 502. The user input elements are configured to control various operational functions of the ambulatory medical device. In such cases, the controller is configured perform the operational functions only in response to actuation of the corresponding user input element(s) of the user interface. For example, the controller may be configured to not perform a given operational function in response to a remote command or signal, or in response to the actuation of any other user input elements of the user interface. Such a configuration may be desirable, for example, where the particular operational function is a critical function that is designed to be activated only by certain inputs, such as a dedicated button on the medical device, to prevent inadvertent or unintended activation by another user input element or remote command. As an illustration, the response buttons (506a and 506b) may be configured to cause a therapy to be delayed or suspended when the buttons are held down together. In such a configuration, the therapy cannot be delayed or suspended when only one of the two buttons is held down or in response to a remote signal.

In some examples, the user input elements are configured to perform other functions, such as selecting parameters, activating diagnostic tests, displaying messages, activating audible alarms, or otherwise interacting with the device 100. In such examples, the functions of the user input elements are not necessarily critical to the medical condition of the patient, and therefore may be remotely reconfigured via a remote communication session as appropriate to perform critical functions in the event that another user input element fails or becomes inoperative. In some examples, the technician can remotely activate any of the user input elements without patient intervention, such as when remotely troubleshooting the device 100.

FIG. 6 shows another example user interface 600, in accordance with an example of the present disclosure. In this example, the user interface 600 can be implemented in a web browser or other graphical user interface application. For example, a web page may be configured to present a virtual user interface 602 to the medical device via a web browser. At least a portion of the user interface 602 is configured to substantially replicate the user interface 408 of, for example, FIG. 5.

In some cases, the user interface 600 can be generated based on data received from the controller 120 via the remote access manager 428, such as when the user interface 600 is connected to the remote system. In this manner, a technician can remotely view and access at least portions of the user interface 408 on the device 100 via the user interface 600 on the web browser.

As can be seen in FIG. 6, the user interface 600 can include an image of the display screen 502' and the user input elements 504' and 506'. In operation, the screen 502' and the user input elements 504' and 506' can mimic the function and behavior of the corresponding screen 502 and user input elements 504, 506a, 506b, such that a user can monitor or control the device 100 remotely. For example, a remote technician may be able to view a sequence of screens corresponding to the sequence of screens being viewed by the patient on the device. To reduce the bandwidth utilized by the data communications interface, the device can be configured to transmit a limited sequence of codes that efficiently represent the information displayed on the screen (or incremental or differential changes in the information), rather than transmitting data representing images of the entire screen on a pixel-by-pixel basis. In such cases, for example, the user interface 600 may include a virtual representation of the user interface 408 generated from the code sequence. Such a virtual representation displayed on the user interface 600 may be visually similar to the screen seen by the patient on the user interface 408, but it will be understood that the user interface 600 may not necessarily display a similar representation.

A user interface of a medical device may include a predetermined set of interactive screens displayed to the patient locally, or the technician remotely, as the case may be, in accordance with device functionality. The patient or technician may navigate, or the device may automatically advance, from one screen to the next based on a state of the device. For example, if the device is performing a diagnostic test that has multiple screens of information and/or user interaction (e.g., a button to activate a step within a multi-step operation, or to acknowledge that the patient or technician has read the information on the screen), the patient or the technician may cause the device to display a different screen by pushing a button or remotely sending a command to advance to the next screen, respectively.

A remote system having the user interface 600, as viewed by a technician, may establish a communications session with the device via the remote access manager 428 and view the same screen the patient is currently viewing or has recently been displayed to the patient, another representation of the screen the patient is currently viewing or has recently been displayed to the patient, the status of the device 100, or other pertinent information about the operation and status of the device. The server may then cause substantially the same screen and status (or other another form of this information) to be displayed to the remote technician based on this information so that the remote technician can work through a device issue while the patient is on the phone with the technician. For example, the user interface 600 of the remote system may display a visually similar representation of the screen as seen by the patient, or the user interface 600 may display information in a different form that represents the information seen by the patient. The user interface 600 may, in one example, indicate which user interface elements (e.g., 504, 506a, 506b in FIG. 5) the patient is activating by lighting up or highlighting the corresponding elements (e.g., 504', 506a', 506b') in the user interface 600, or displaying a message (e.g., in textual command interface 608) that a particular element is being activated. If the user is attempting to activate a user interface element, the remote system may indicate whether or not the user interface element is operating correctly (e.g., patient says he is pressing a button but the button does not show activation on the remote system). In this manner, the remote technician may troubleshoot the device by asking the patient to activate certain user interface elements and monitoring the user interface 600 of the system to see if the device responds accordingly.

In another example, the remote technician may type or draw on the user interface 600, and the typing or drawing will be sent to the device and displayed on the local user interface for the patient to see. For example, for demonstration or tutorial purposes, the remote technician may use a cursor or touch screen on a remote computer system operatively connected to a server. The server may then cause the cursor and related information (e.g., x-y coordinates of the technician's cursor and/or one or more codes representing a current graphical interface and corresponding state within a given state machine) over the communications session to the device, which causes the device to draw a cursor for guiding the patient through the operation of the device. In another example, the remote technician may remotely force the device to display certain screens on the local user interface for the patient to view. For example, if the technician is guiding a patient through the steps of how to respond to a therapeutic shock, the technician can cause certain screens to be displayed that the patient will ordinarily see in normal operation. In some examples, the functionality variously described in this paragraph may be protected by security so as to require permission from the patient before the remote technician is allowed to view or otherwise control the device remotely. As the remote technician interacts with the user interface 600, in some examples, the remote system can send a command to effect a same or substantially same change to the corresponding device screen.

In some implementations, a technician may cause one or more training modules to be deployed to the medical device for training and/or demonstrating one or more features of the medical device. For example, the modules may be deployed as preconfigured executable scripts that are delivered to the medical device over a remote communication session. The scripts can be executed by the device to present a guided tutorial or other information to the patient via the user interface. In certain implementations, some modules may be preloaded on the medical device, and remotely activated via the communication session. For example, one or more of the following training modules may be provided in this manner: a treatment/siren alarm module, an after-treatment module, a response button module, a gong alert module, electrode falloff module, garment care and maintenance module, battery charge and maintenance module, among others. Each module can be in the form of one or more media types or a mix of media (e.g., slides with images, videos, text, and/or audio content) and vary in levels of technical sophistication.

The technician can activate a technical support mode or other demo mode of the device over the remote communication session. In such implementations, medical devices like external ambulatory therapeutic devices (e.g., defibrillator) can be configured to continue monitoring the patient for underlying medical conditions that the device can treat (e.g., cardiac arrhythmias). As such, even if a remote communication session is ongoing, the device is configured to carry out its critical functionality without interruption.

In implementation, once the remote communication session is activated a two-way communication path is established. The technician can remotely control the sequence, operation, and timing of the training modules over the path. For example, the remote server can send instructions in the form of, for example, XML or JSON code, to control the content and duration of display of the training module media.

Figure 10:
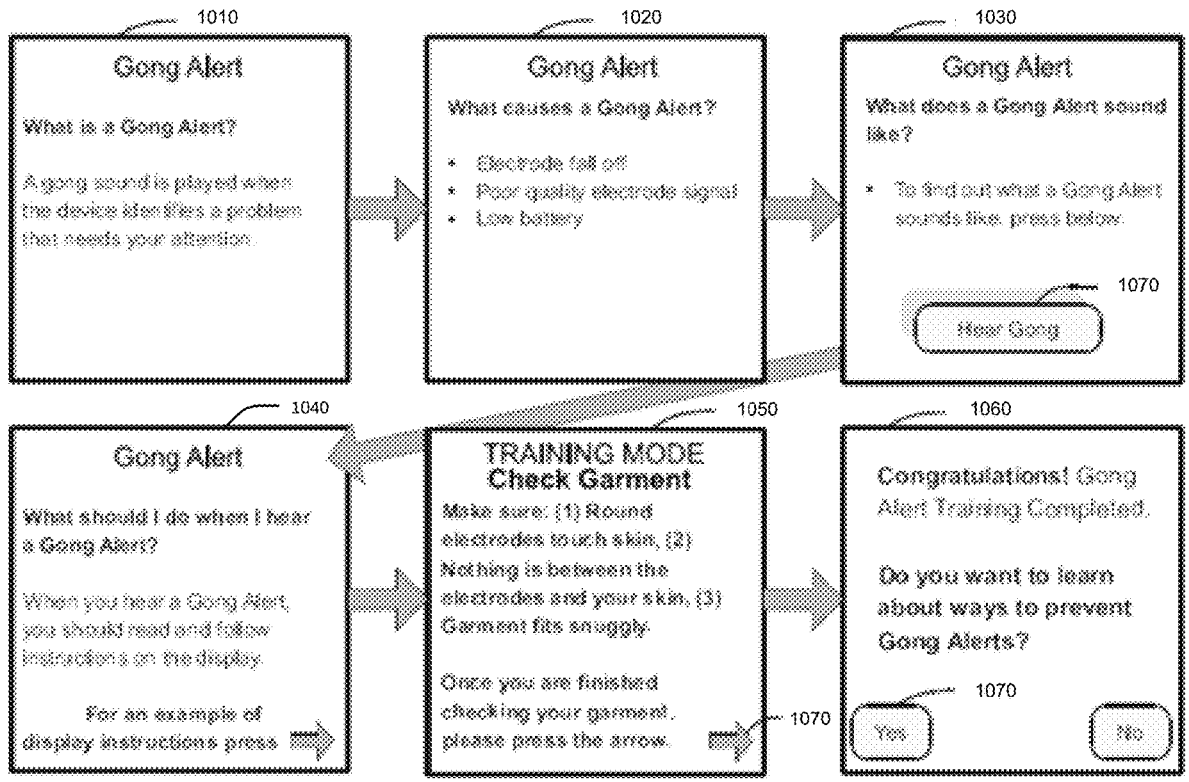
FIG. 10 shows several screen shots of an example training module for a medical device, in accordance with an example of the present disclosure.

FIG. 10 shows several screen shots of an example training module for a medical device, in accordance with an embodiment. As shown, the device can be configured to display a sequence of informational and interactive screens for guiding a patient through the training module. For example, the first screen 1010 may display information about a particular feature (e.g., a gong alert) of the device. The remote server may then cause the second screen 1020 to display when the remote technician requests it remotely. The third through sixth example screens 1030, 1040, 1050, 1060 each include one or more interactive elements 1070 that the patient may activate to perform an operation within the training module, such as advancing to the next or previous screen, or activating a feature of the device (e.g., play a gong sound or start an optional section of the training module). Other examples of training modules are described in U.S. Provisional Patent Application Ser. No. 62/235,883, entitled "Training Modules for External Medical Device" and filed on Oct. 1, 2015, which is incorporated herein by reference in its entirety.

In some examples, as shown in FIG. 6, the user interface 600 includes additional elements that can be used to remotely monitor or control the device, such as buttons 604, alarm status 606, and a textual command interface 608. These additional elements may not necessarily be available to the patient via the user interface 408, but enable a technician to interact with the device 100 in several ways. For example, the buttons 604, when activated by the technician, may initiate or terminate a remote connection with the device 100, cause the device 100 to execute a diagnostic test, retrieve and display an operational status of the device 100 in the user interface 600 (e.g., display an event or alarm history, the amount of time the patient has been wearing the device, or other device information in the alarms region 606), activate or deactivate a remote control function, or any combination of these or other relevant functions. In some examples, the user interface includes the textual command interface 608, which enables the technician to type commands using a keyboard, and send the commands to the device 100, as well as to view information received from the device 100, such as responses to the commands. In some cases, the textual command interface 608 enables the technician to interact with the device 100 in real time or near real time for troubleshooting purposes.

Example Use Case

Figure 7:
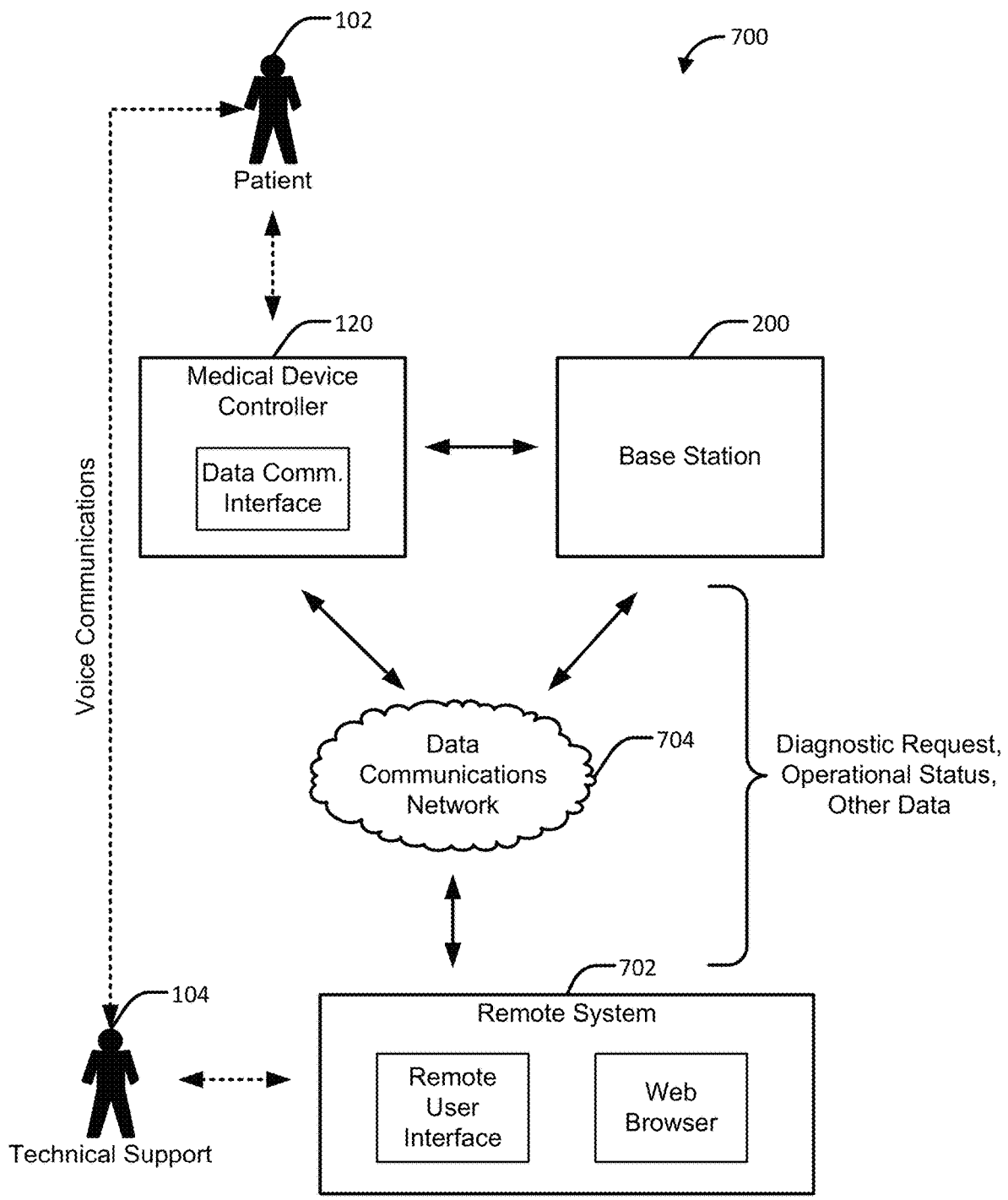
FIG. 7 shows an example system, in accordance with various examples of the present disclosure.

FIG. 7 shows an example system 700 in accordance with various examples. In the system 700, the system is configured to provide remote access to an ambulatory medical device including the device medical device controller 120 and data communications interface 406 of FIG. 4. In addition to the controller 120, the system 700 includes an optional base station 300 of FIG. 3, a remote system 702, and a data communication network 704. In some examples, the controller 120 can include an application, browser, email client, or some other local component configured to communicate with the remote system 702 via the network 704. In some implementations, the controller 120 may communicate with the network 704 and the remote system 702 via the base station 300 as described herein. The controller 120 is configured to transmit data to, and receive data from, the remote system 702 via the network 704. Such data may, for example, include a request to perform a diagnostic test, a request to establish a communication session with the remote system 702, a request to reconfigure the user interface of the ambulatory medical device, data representing an operational status of the device, and other data representing control and monitoring functions of the device, such as variously described in this disclosure. The remote system 702 can include a remote user interface, such as the user interface 600 of FIG. 6, and a web browser or other application configured to render at least a portion of the remote user interface. The network 704 may include any communication network through which programmable devices may exchange information. In some examples, the network 704 supports wireless network and/or wired connections. For instance, the network 704 may support any of various networking standards such as GSM, CMDA, USB, BLUETOOTH, CAN, ZigBee, Wireless Ethernet, and TCP/IP among others.

The medical device may include any medical device disclosed herein such as an ambulatory external defibrillator or a cardiac monitor, or another medical device that includes the controller 120 of FIG. 4 or similar components. In some examples, the medical device can be associated with, and provides care to, a patient 102. As shown in FIG. 7, the medical device may provide information to a patient 102, a technician 104, or other individual. The technician 104, who is capable of providing the patient 102 with assistance in the operation and troubleshooting of the device, can interact with the controller 120 via the remote system 702. Further, the technician 104 can communicate directly with the patient 102 via a telephone or Internet telephony while contemporaneously providing technical assistance via the remote system 702. For example, the technician 104 may ask the patient 102 to describe the behavior of the medical device or to press a button on the controller 120 while speaking with the patient 102 by telephone.

In some examples, the information presented to the patient 102 via the user interface of the controller 120 varies depending on a severity of a fault or an operational status of the device. In some implementations, the device may be configured to determine the severity of the fault based on the information below and relay a corresponding service code and information about one or more actions taken in response to the fault. The device may then determine, based on the severity of the fault, whether to initiate or prompt the patient to initiate the remote communication session to allow for a remote technician to service the fault.

In one example, anomalous operational statuses are categorized into two groups, e.g., Group One and Group Two based on severity. For example, Group One status can be reflected through use of service codes that have a "1" prefix (e.g., service codes "101", "102", and so on). When the medical device is in a Group One, or non-critical status, the patient can continue to use the medical device as prescribed. When the medical device is in a Group Two, or critical status, the patient may need to immediately seek assistance with (e.g., assistance from a service technician or health care professional) and/or discontinue use of the medical device. For example, Group Two status can be reflected through use of service codes that have a "2" prefix (e.g., service codes "201", "202", and so on). For example, when the medical device has a Group Two type critical issue, the patient may be presented with a screen indicating that the device had suffered a serious problem that could prevent patient treatment operations from occurring. For example, a therapeutic device such as an ambulatory external defibrillator may not be performing monitoring or treatment operations in such a status. Similarly, a cardiac or other physiological monitoring device may not be performing patient monitoring in such a status. The device may include other statuses, groups, or levels of fault severity. In some implementations, a subset of faults involving, for example, the communications module, may trigger different service codes than Group One or Group Two service code. For example, communication faults may be assigned to Group Three, and as such the corresponding service codes may use a "3" prefix. While numeric service codes and/or use of prefixes are described herein, other types of codes, formats, or symbols may be possible without deviating from the scope of the disclosure.

When displaying information about a Group One status, which includes less severe, non-critical, anomalous operational statuses, the device may provide the patient, via the user interface, with specific information about the detected anomaly and its most likely cause(s), along with a message directing the patient to contact a technical assistance representative while continuing to use the medical device. The technician 104 may, from the remote system 702, then remotely retrieve information about the status of the device and/or view the user interface of the device. Example Group One status issues can include one or more of the following: connection to a base station or other remote server is taking too long (e.g., exceeds a predetermined connection time threshold), such connection may have temporarily failed, another data transfer or remote communication session may already be in progress, there may be excessive noise on one or more physiological sensors, the battery may have reached critical charge level and needs to be recharged or changed, one or more portions of the garment may be improperly adjusted and needs to be re-adjusted, and one or more components of the electrode system may have been improperly assembled. In some implementations, other example non-critical operational status of the ambulatory medical device comprises at least one of the following: a connection to a remote computing device (e.g., remote computing device 1204 of FIG. 12 below) exceeds a predetermined connection time threshold, the connection to the remote computing device may be deemed to have temporarily failed, or another data transfer or remote communication session may already be in progress.

Figure 11:
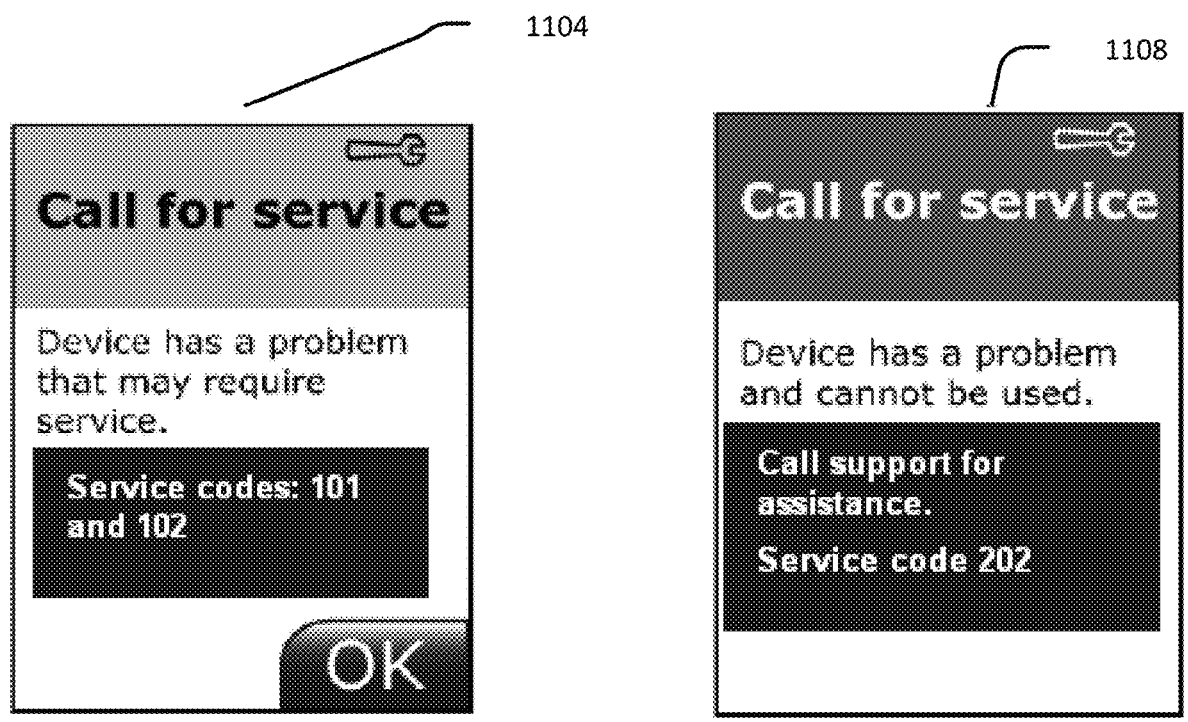
FIG. 11 shows example screens displayed on a medical device, in accordance with an example of the present disclosure.

When a device fault occurs, the device is configured to determine that the type of fault is a Group One fault (non-critical fault). For example, if a pulse truncation fault, charge profile fault, or a gel fire fault is detected, the device can trigger a corresponding service code. For example, as noted in the table below, the pulse truncation fault may be assigned service code 101. When such a fault is detected, the device may take no immediate action. However, on the next device power up, the device may display a screen informing the patient that the monitor needs to be serviced. Following the notification, the device may be configured to resume normal operation. Similarly, when a charge profile fault is detected, the device may be configured to take no immediate action as long as there is sufficient energy to deliver a pulse to the patient, if needed. The device may further provide instructions to the patient indicating that the operational status or fault is a non-critical operational status or fault, and/or the patient may continue use of the device contact a remote technician. As such, the device may be configured on next power up to display a screen informing the patient that the monitor needs to be serviced. An example of such a "Call for service" screen 1104 is shown in FIG. 11. As before, following the notification, the device may be configured to resume normal operation.

In an implementation, after the patient calls the remote technician for service, the device can be remotely entered into a technical support mode as discussed above. The remote technician can then remotely address the issue that led to the service code being declared. In some examples, the remote technician can use the technician support mode to guide the patient (and/or a support person) through one or more steps relating to the medical device, e.g., steps to help restore the operational status of the medical device. For example, the remote technician can use the user interface to show the patient how to adjust one or more sensors, re-adjust the garment, or detach and re-attach the device battery.

Example Group One status service codes are shown in Table 1 below, along with proposed actions to be taken for each of the service codes. The table also shows a general description of the corresponding service code (e.g., a description of the fault), an action taken or to be taken by the device, an action taken or to be taken by the device the next time the device is powered-up, and a disposition (e.g., an action taken by the remote technician).

TABLE 1

Group One Status List

| Service code | General description | System action | Action on next power-up | Disposition (e.g., action by remote technician) |
|---|---|---|---|---|
| 101 | Pulse truncation fault | None | Service code 101 followed by normal operation | Controller or Monitor service required |
| 102 | Charge profile fault | None if pulse energy is available Display "Call for help" is no pulse energy available | Service code 102 followed by normal operation | Controller or Monitor service required |
| 103 | Gel fire fault | None | Service code 103 if attached electrode assembly indicates gel fire fault | Electrode assembly service required |
| 104 | A non-critical memory fault (e.g., an SD Card Fault) | None | Service Code 104 followed by normal operation | Controller or Monitor Service Required |
| 105 | Pulse Test Relay Stuck | Service Code 105 followed by normal operation | If problem continues - Service Code 105 followed by normal operation | Controller or Monitor Service Required |
| 106 | Multiple Battery Capacity Test Failures | Service Code 106 followed by normal operation | If problem continues - Service Code 106 followed by normal operation | Battery Service Required |
| 107 | Multiple Abnormal Shutdowns | Service Code 107 followed by normal operation if possible | Service Code 107 followed by normal operation | Controller or Monitor and electrode assembly service required |
| 108 | Non-Critical Database Error | None | Service Code 108 followed by normal operation | Controller or Monitor Service Required |
| 109 | File System Unlocked | None | Service Code 109 followed by normal operation | Controller or Monitor Service Required |
| 110 | Over Voltage Cleared No Energy | See code link for more detail | Service Code 110 followed by normal operation | Controller or Monitor Service Required |
| 111 | Old Data Files on SD Card | See code link for more detail | Service Code 111 followed by normal operation | Controller or Monitor Service Required |
| 112 | Corrupt Questionnaires Database | Disables Questionnaire/Heart Walk and their setup | Service Code 112 followed by normal operation | Controller or Monitor Service Required |

TABLE 1-continued

Group One Status List

| Service code | General description | System action | Action on next power-up | Disposition (e.g., action by remote technician) |
|---|---|---|---|---|
| 113 | Parameters Database Restored from Backup | Recent changes to Parameters Database not saved | Service Code 114 followed by normal operation | New Patient Setup Required to Clear |

For example, the technician 104 may ask the patient 102 to make adjustments to the device 100 while monitoring the user interface via the remote system 702. Additionally or alternatively, the technician 104 may remotely access the device and attempt to resolve the problem on behalf of the patient 102 by sending one or more commands to the device from the remote system 702. For example, the technician may remotely reset the device, adjust a setting of the device, or initiate a remote reboot of a specific functionality or the entire device, or perform a software update or reinstall of a specific functionality or the entire device. For example, Group One statuses may be reset by the patient manipulating the medical device in some predetermined manner (e.g., pressing an acknowledgment button to acknowledge the event, rebooting the medical device by pressing a reset button, turning a power switch on and off, or removing and reinserting the same battery or a new battery, etc.), according to instructions provided by the technician 104 over the telephone. As another example, the technician may remotely access the device and reconfigure patient-specific parameters, defaults or preferences. For example, a technician may reconfigure the user response interface to provide alternative user response elements where the diagnostic test indicates a fault with the default response elements, or provide additional user response elements or configurations according to patient preference.

When displaying information about a Group Two status (critical faults), which includes more severe anomalous operational statuses, the device may provide the patient, via the user interface, with specific information about the detected anomaly and its most likely cause(s), along with a message directing the patient to immediately contact a technical assistance representative. In such a case, the technician 104 may remotely verify the problem by accessing the device, and upon confirming the problem or if the device is nonresponsive, inform the patient that the device needs to be replaced immediately. For example, if a remotely triggered diagnostic test of the converter circuitry fails, the technician may immediately be able to see the results of the test and inform the patient that the device needs to be replaced immediately. Group Two statuses cannot be reset because, in such cases, the device is deemed to be non-operational due to failure of a specific test. In addition, in some implementations, the device may provide the patient, via the user interface, with additional information when reporting an anomalous operational status belonging to Group Two. This additional information may include directions for the patient to follow immediately, such as to replace a component of the medical device that is serviceable by the patient or to remove the device from the patient and discontinue use of the device until the device is repaired.

When a device fault occurs, the device is configured to determine that the type of fault is a Group Two fault (a critical fault). For example, if a response button is stuck or the patient parameters become corrupted, the device can trigger a corresponding service code which may indicate that the device is unusable. For example, as noted in the table below, the response button stuck fault may be assigned service code 201. When such a fault is detected, in some examples, the device may cause itself to be immediately disabled. On the next device power up, the device may display a screen informing the patient that the monitor needs to be serviced. An example of such a "Call for service" screen 1108 is shown in FIG. 11. For example, such a screen may also include a warning to the patient to discontinue use of the device and contact a support or a remote technician. As shown, the screen may inform the patient that the patient may call technical support for assistance. The device may remain disabled and continue to display screen 1108 until the device has been returned for service.

Example Group Two status service codes are shown in Table 2 below, along with proposed actions to be taken for each of the service codes. The table also shows a general description of the corresponding service code (e.g., a description of the fault), an action taken or to be taken by the device, an action taken or to be taken by the device the next time the device is powered-up, and a disposition.

TABLE 2

Group Two Status List

| Service code | General description | System action | Action on next power-up | Disposition (e.g., action taken by the remote technician) |
|---|---|---|---|---|
| 201 | One or more response buttons stuck, or response button signal error | System Disabled | Service Code 201 if problem continues, normal operation if problem resolved | Controller or Monitor Service required if problem continues |

TABLE 2-continued

Group Two Status List

| Service code | General description | System action | Action on next power-up | Disposition (e.g., action taken by the remote technician) |
|---|---|---|---|---|
| 202 | Patient Parameters Corrupt | System Disabled | System Disabled-Service Code 202 | Controller or Monitor Service Required |
| 203 | Pulse Test Fault (e.g., the device is unable to charge and deliver a pulse to an internal test load) | System Disabled | System Disabled-Service Code 203 | Controller or Monitor Service Required |
| 204 | Electrode assembly/ Controller or Monitor inoperative | System Disabled | System Disabled-Service 204 if electrode assembly not replaced, Service 204 if Controller or Monitor problem, normal operation if electrode assembly replaced and Monitor not the problem | Electrode assembly and Controller or Monitor Service Required |
| 205 | Audio-visual Messaging Data Corrupt | System Disabled | System Disabled-Service Code 205 | Controller or Monitor Service Required |
| 206 | Shell Application MD5 Failed | System Disabled | System Disabled-Service Code 206 | Controller or Monitor Service Required |
| 207 | Patient parameters Update Fault | System Disabled | System Disabled-Service Code 207 | Controller or Monitor Service Required |
|  | Invalid Operating Mode | System Disabled | System Disabled-Service Code 208 | Controller or Monitor Service Required |

Example Methodologies

Figure 8:
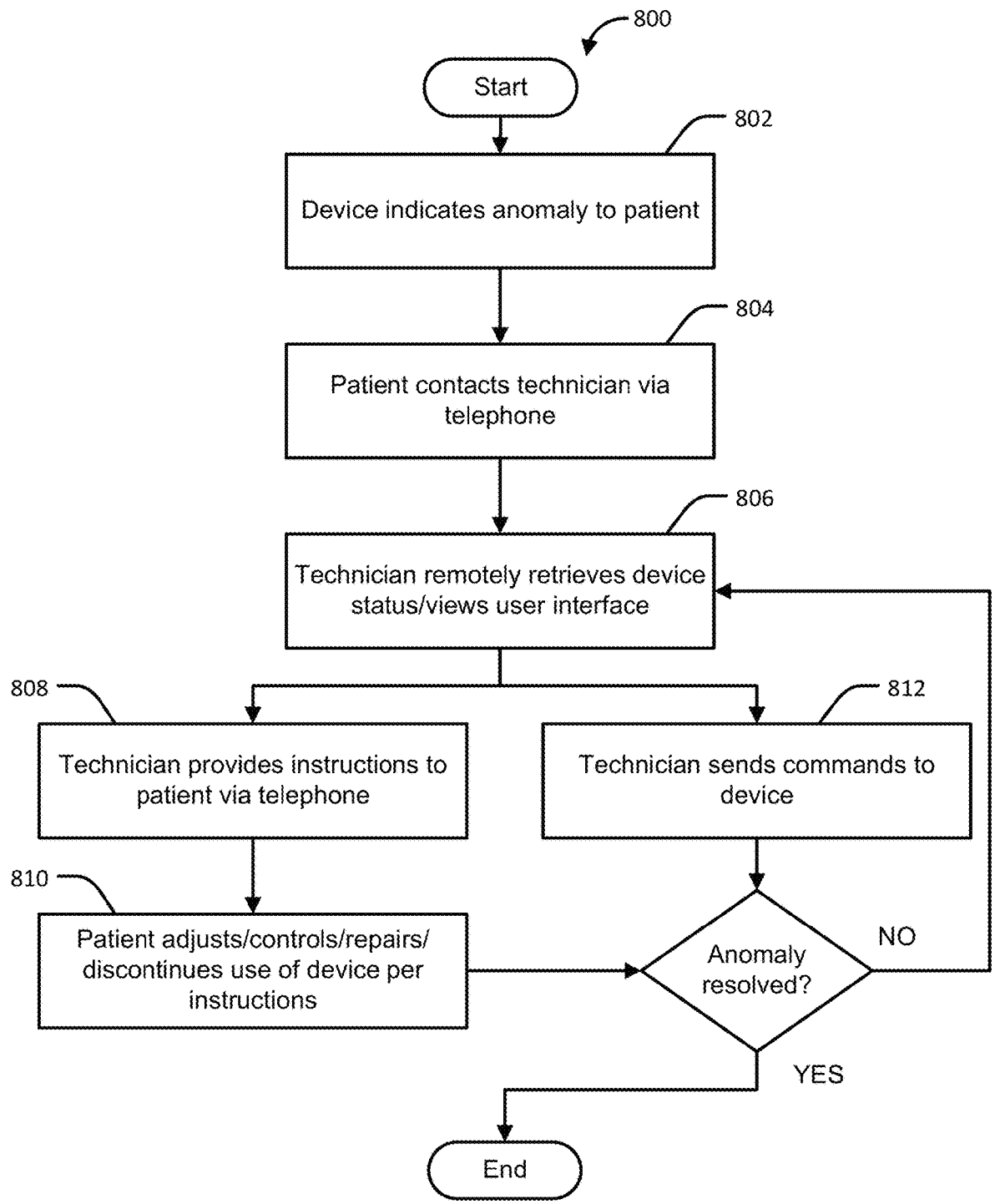
FIG. 8 shows an example device diagnostic test process flow that can be used in conjunction with a medical device, in accordance with an example of the present disclosure.

FIG. 8 shows an example device diagnostic test process flow 800 that can be used in conjunction with an ambulatory medical device, in accordance with an example of the present disclosure. Initially, the device indicates 802 an anomaly to a patient who is using the device. The indication may result, for example, from one of the diagnostic tests discussed with respect to FIGS. 4-7. The indication can include information about the anomaly and a direction for the patient to call a technician for assistance. The patient then contacts 804 the technician via telephone. The technician may ask the patient questions to gather information for troubleshooting and resolving the anomaly. The technician then remotely retrieves the status of the device 806 or other diagnostic information, and/or views the user interface of the device remotely. Retrieving the status may include, for example, sending diagnostic test commands to the device and viewing the results, viewing the event or alarm history stored in the device, viewing the operating parameters of the device, or any combination of these or other suitable actions. For example, if the patient has encountered a "Call for service" screen (e.g., screens 1104 and 1108) with a corresponding service code, the device status information may include the service codes (see, e.g., Tables 1 and 2 above). The remote technician may also be able to interrogate the device to retrieve information about any actions taken by the patient and/or the device in response to the service codes.

In some cases, after remotely retrieving the status of the device 806, the technician can provide instructions 808 to the patient via telephone. For example, the technician may direct the patient to press a button to reset the device, adjust a sensor, replace a battery, or discontinue use of the device, depending on the nature of the anomaly and the appropriate actions for resolving the anomaly. Then the patient can adjust, control, repair or discontinue use 810 of the device per the instructions. If the actions of the patient resolve the anomaly, then the method 800 ends. Otherwise, the technician can continue to remotely retrieve the status of the device 806 or view the user interface.

In some cases, after remotely retrieving the status of the device 806, the technician can send one or more commands 812 to the device. For example, the technician may send a command to reset the device, to perform a diagnostic test on the device, or to control the device remotely without intervention by the patient. If the actions of the technician resolve the anomaly, then the method 800 ends. Otherwise, the technician can continue to remotely retrieve the status of the device 806 or view the user interface.

Figure 9:
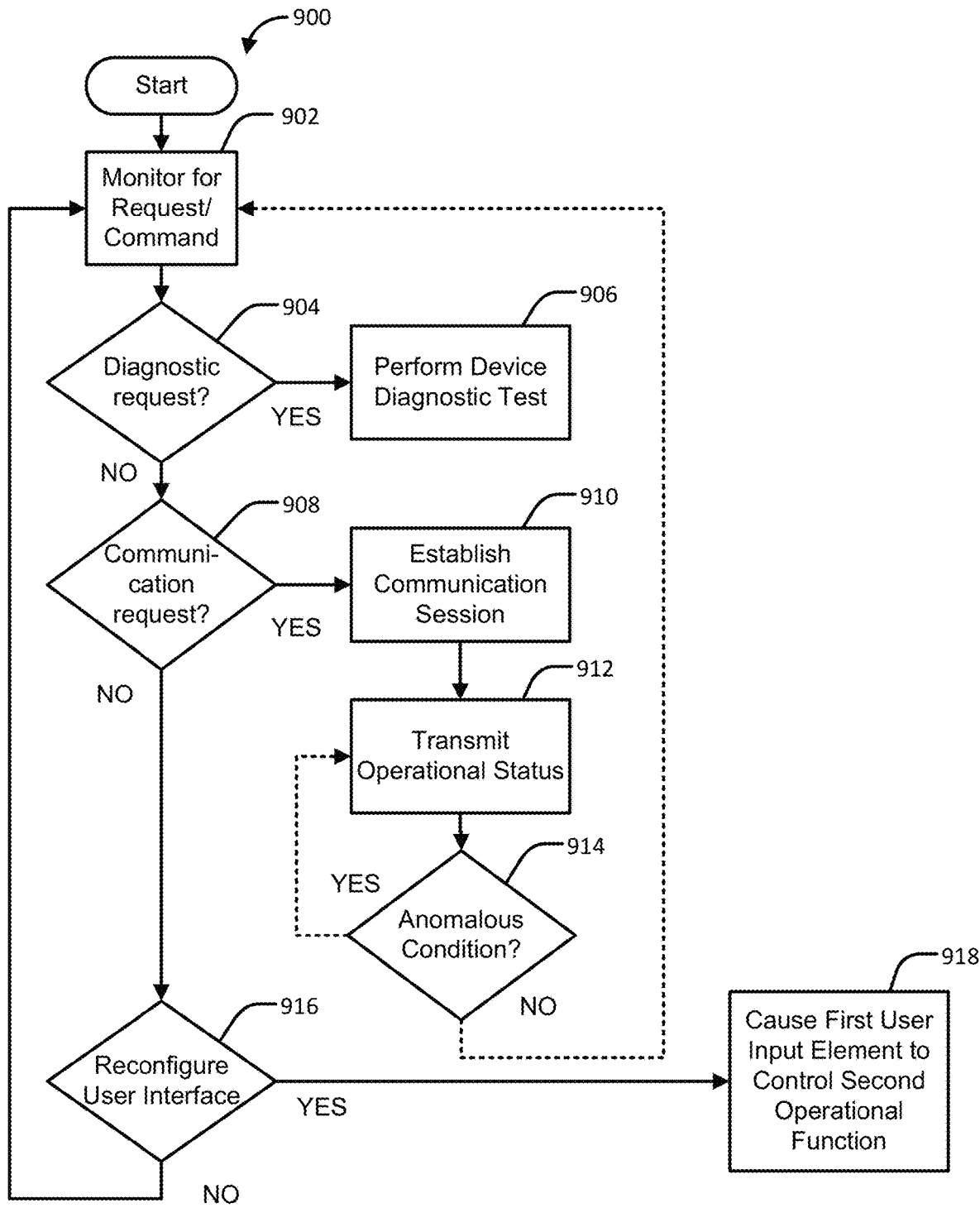
FIG. 9 shows a flow diagram of an example methodology for remotely controlling or determining the status of a medical device, in accordance with various examples of the present disclosure.

FIG. 9 shows a flow diagram of an example methodology 900 performed by an exemplary system for remotely controlling or determining the status of an ambulatory medical device, in accordance with various examples of the present disclosure. For example, methodology 900 can be implemented and/or performed by the medical device and/or system (e.g., controller 120 and associated components forming the medical device and/or system). For instance, in one example, the methodology 900 can be performed by the remote access manager 428 of FIG. 4, in conjunction with any other element of the medical device controller 120. The methodology 900 includes monitoring 902 for a request 904 from a remote system. In some examples, the ambulatory medical device includes, or is configured to be coupled to, a base station configured to communicate with the controller. In some examples, the request from the remote system includes a text message received over at a fixed line telecommunications network or a mobile telecommunications network. In either such examples, the request from the remote system can be routed to the controller via the base station or a mobile device.

When executing the act of monitoring 902 in some examples, the remote access manager 428 is configured to operate in a low power mode or a normal power mode. In some such cases, the remote access manager 428 is configured to periodically monitor for a diagnostic test command less frequently while operating in the low power mode than while operating in the normal power mode to conserve power. For example, the base station may receive and buffer a diagnostic test command or other command from the remote system until the remote access manager polls the base station for such command. In a normal power mode, every few minutes (e.g., every 1 minute, 5 minutes, 10 minutes, 15 minutes, etc.), the remote access manager 428 can cause the medical device to poll the base station via a wireless connection for a buffered request or command. In a low power mode, the frequency may be increased to 30 minutes, 1 hour, or more. In an implementation, instead of or in addition to polling a local base station, the medical device may poll a remote computer system or server application for such buffered commands.

In some implementations, the medical device may itself be configured to be in a low power mode (e.g., certain functionality of the device may be inactive, such as, user interface, data communications, etc.). For example, in certain implementations, the ambulatory medical device is configured to consume less power while operating in the low power mode than while operating in the normal power mode. For instance, while operating in the low power mode, certain functions of the device that are not needed at all times (e.g., the user interface, and the data communications interfaces) may be temporarily disabled or may temporarily operate less frequently than in the normal power mode so as to conserve battery power. In such implementations, the remote access manager 428 can be configured check for a buffered command at a predetermined frequency (e.g., every 1 minute, 5 minutes, 10 minutes, etc.) and then cause the medical device to reenter the low power mode until the next polling interval has elapsed if no buffered request or command is available. If such a request or command is available, the remote access manager may retrieve the request or command and perform the corresponding diagnostic test or other action, accordingly.

In some examples, the request from the remote system is a request to perform a diagnostic test, which causes the controller to perform the diagnostic operation 906 in response to the request. Examples of the diagnostic test include requesting the last time a converter or capacitor has been charged or tested, or performing an audio test. In some cases, the remote access manager is further configured to transmit data representing an operational status of the ambulatory medical device to the remote system. In some cases, the operational status of the controller results from performing the diagnostic test (e.g., the operational status may include the results of the diagnostic test, such as pass or fail, or the values of certain parameters that indicate whether the device is operating normally or abnormally). However, the operational status of the controller can include other information not resulting from the diagnostic test, such as device identity, run time, patient wear time, event history, alarm history, or other information that is generated by the controller. In some cases, the remote access manager is further configured to send the data representing the operational status of the ambulatory medical device in real time or substantially in real time, although it will be understood that the data can be sent at any time. For example, the diagnostic test may be performed in real time (e.g., as soon as the request is issued by the remote system and received by the device), or delayed (e.g., at some point in time after the request is issued by the remote system, such as when the request is buffered in the base station before being transmitted to the device). In some cases, the remote access manager is further configured to detect an anomalous condition of the controller, and to transmit data representing an operational status of the ambulatory medical device to the remote system in response to detecting the anomalous condition.

In some examples, the data representing the operational status of the ambulatory medical device includes a web page configured to present a virtual user interface to the ambulatory medical device via a web browser, such as shown and described above with respect to FIG. 6. For example, the data may be used to generate, in the web browser, a virtual copy or other representation of the user interface of the device to enable a technician to remotely view and interact with the device. The virtual copy or other representation of the user interface, as viewed by the technician, may be visually similar to the local user interface as seen by the patient, however it will be understood that the user interface presented to the technician may include more or less information than presented to the patient, and that the information may be displayed by the web browser in a different format or arrangement on the screen than in the local user interface.

Referring again to FIG. 9, in one example, the request from the remote system is a request 908 to communicate with a remote system, which establishes a communication session 910 with the remote system in response to the request. In some cases, the remote access manager is further configured to transmit data representing an operational status of the ambulatory medical device 912 to the remote system via the communication session. In some such cases, the data representing the operational status of the ambulatory medical device is transmitted in response to the request. In some such cases, the remote access manager is further configured to detect an anomalous condition 914 of the controller, and to transmit the data representing the operational status of the ambulatory medical device 912 to the remote system via the communication session in response to detecting the anomalous condition. In some cases, the remote access manager is further configured to transmit the data representing the operational status of the ambulatory medical device in real time or substantially in real time, although it will be understood that the data can be sent at any time. In some cases, the data representing the operational status of the ambulatory medical device includes a web page configured to present a virtual user interface to the ambulatory medical device via a web browser, such as described above with respect to FIG. 6.

Referring again to FIG. 9, in one example, the user interface includes at least two user input elements (e.g., the elements 506a and 506b of FIG. 5). One of the user elements is configured to control an operational function of the ambulatory medical device, and another one of the user input elements is configured to control another operational function of the ambulatory medical device. In some cases, request from the remote system is a command to reconfigure the user interface 916. In such cases, the controller is further configured to reconfigure the user interface 918 to cause one of the user input elements to control another operational function instead of the original operational function of that user input element. In some such cases, one of the user input elements is in an anomalous or inoperative condition.

As mentioned above, in some examples, the user interface 408 includes at least two user input elements (e.g., physical switches 506a and 506b, virtual button 504, or any combination of these). The user input elements may be configured to control the same operational function of the ambulatory medical device 100. For example, both of the user input elements (e.g., buttons 506a and 506b) may be configured as a response buttons that when depressed indicates to the controller 120 that the patient is conscious, which causes the controller 120 to withhold the delivery of therapeutic defibrillating shocks in the event of a detected cardiac event. As noted above, a failure of the user input element (e.g., button 506a) may pose a serious risk to the patient. To this end, in some examples, the controller 120 is further configured to reconfigure the user interface 408 to cause one of the user input elements (e.g., 506b) to control the same operational function as another one of the user input elements (e.g., 506a). Such a reconfiguration may be desirable, for example, when one of the user input elements (e.g., user input element 506a) is experiencing a malfunction or is otherwise inoperative, so that another user input element (e.g., user input element 506b) can be used at least temporarily to supplant the inoperative user input element (e.g., user input element 506a). In another example, if one of the user input elements 506a is configured to cause Function A to be performed when the user input element 506a is activated by the patient, and another one of the user input elements 506b is configured to cause Function B to be performed when the user input element 506b is activated by the patient, then the controller 120 may reconfigure the user input element 506b to perform Function A instead of Function B, or vice versa. Such reconfiguration of the user interface 408 can remain in place indefinitely, or at least until the inoperative portion of the user interface 408 is repaired.

The processes disclosed herein each depict one particular sequence of acts in a particular example. The acts included in these processes may be performed by, or using, one or more computer systems specially configured as discussed herein. Some acts are optional and, as such, may be omitted in accord with one or more examples. Additionally, the order of acts can be altered, or other acts can be added, without departing from the scope of the systems and methods discussed herein. Furthermore, as discussed above, in at least one example, the acts are performed on a particular, specially configured machine, namely a medical device configured according to the examples disclosed herein.

Mobile-based Communication Systems

As described above, in an implementation, the controller 120 is in data communication with one or more remote computing devices (e.g., mobile remote computing device 317 of FIG. 3). In some examples, a remote technician may access the controller 120 over a remote communication session established between the medical device controller 120 and the mobile remote computing device 317.

Figure 12:
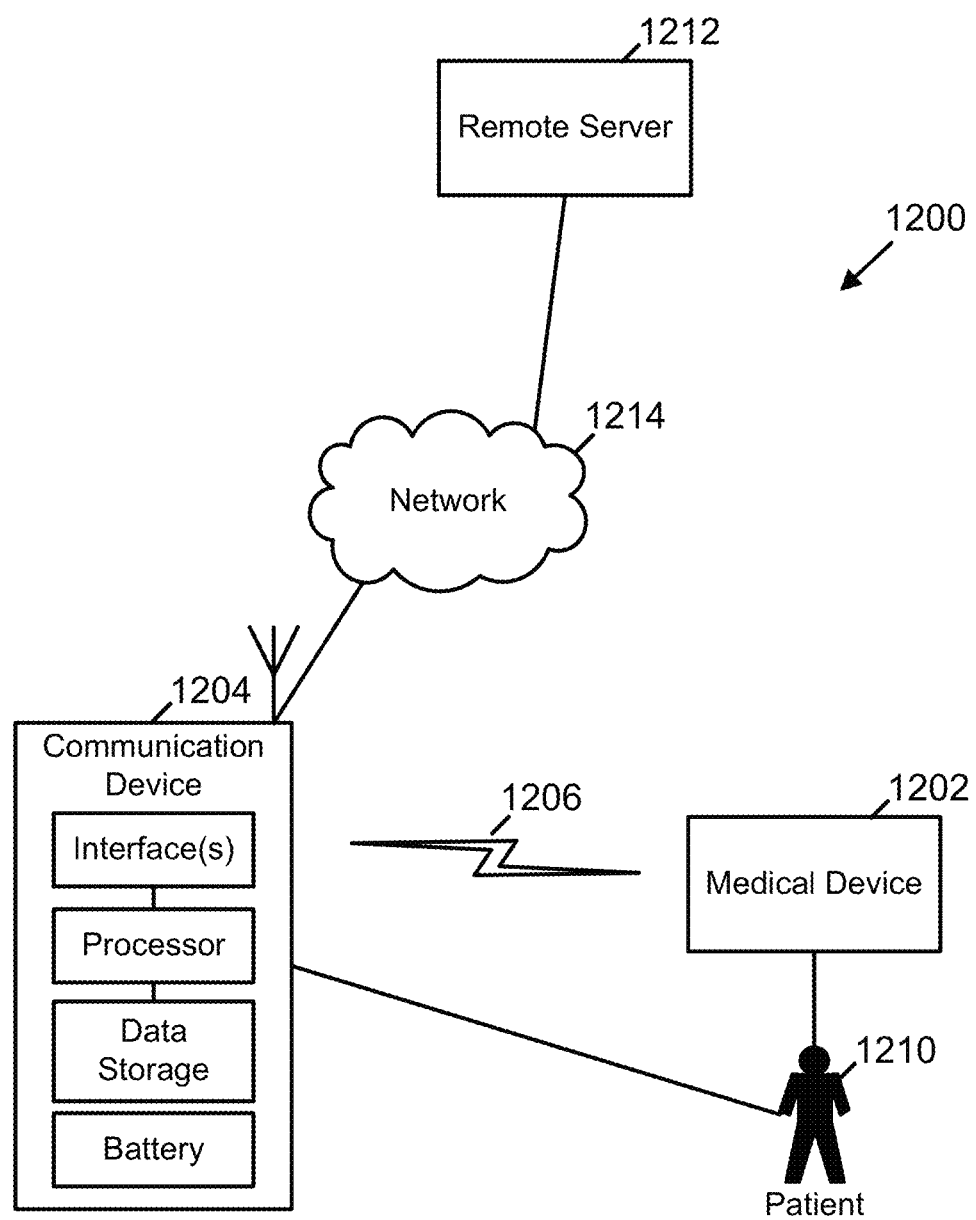
FIG. 12 shows an example system involving a remote computing device, in accordance with various examples of the present disclosure.

FIG. 12 illustrates a remote diagnostic system 1200 in accord with some of these examples. As shown, the remote diagnostic system 1200 includes a medical device 1202, a remote computing device 1204, a remote server 1212 (e.g., accessible to a remote technician via a workstation), a network connection 1206 and a communication network 1214. The medical device 1202 exchanges information with the remote computing device 1204 via the network connection 1206. Similarly, the remote computing device 1204 may exchange information with the remote server 1212 via the network 1214. In at least one example, the remote server 1212 can be configured to deploy or download one or more components (e.g., programs or "apps") to the remote computing device 1204 that cause the remote computing device 1204 to transmit particular commands to the medical device 1202. In some implementations, the remote server 1212 can be configured to deploy or download the one or more components to the medical device 1202 (e.g., containing the controller 120).

The medical device 1202 may include a controller 120 implementing a remote access manager 428 as shown in FIG. 4. For example, the remote access manager 428 may be implemented as a limited functionality component for facilitating the interactions shown in FIG. 12. In some implementations, the remote computing device 1204 may be releasably secured and/or coupled into a receptacle of the base station.

In an implementation, a plug-in or application can be deployed or downloaded on the medical device 1202 and/or the remote computing device 1204 to process data, returning only the results, in order to save data usage. As such, a remote technician may cause the plug-in to be deployed or downloaded over a remote communication session and receive the results of the data in real time or substantially real time. For example, a software module (e.g., an extensible application programming interface or API) can be provided on the controller 120 that is controlled by the remote computing device 1204 in a secure and limited way. The limited functionality module can be configured to be limited in its functionality such that it operates within the environment of the controller 120 but is unable to affect the controller's 120 critical functionality. For example, in an implementation where the remote computing device 1204 is a non-medical device such as a smartphone, an app may be provided on the smartphone to control the limited functionality software module of the controller 120. The app may seamlessly receive instructions from the remote server 1212 and cause one or more of the instructions to be executed on the medical device 1202. The remote technician may then access the app and cause the app to execute instructions on the limited functionality software module of the controller 120.

For example, the module may not be permitted to alter or effect changes to any of critical device functions, such as treatment parameters, critical device self-tests, and power management. The module may, however, be permitted to write certain messages to the controller 120's user interface, for example, at predetermined times, or enable one or more alerts mechanisms. For example, it may be desirable to remind a patient to take his/her medication at a prescribed time. The instructions may be sent to the limited functionality module by the remote controller when the device is within range of the controller. The module's access to the rest of the monitor software can be securely limited by only enabling certain API-functionality. For example, the module may receive commands from the remote device relating to providing statuses of certain device parameters without being able to change any of the parameters. For example, the module may be able to provide device status(es), electrode(s) status(es), battery information, etc.

For example, the module may be able to issue instructions relating to a patient's rehabilitation (directed rehabilitation) at predetermined times. For example, the module may be able to monitor a patient's compliance with the instructions and report back information relating to the patient's compliance.

Additional details regarding the configuration of the remote computing device 1204 and/or the medical device 1202 can be found in described in U.S. Patent Application Ser. No. 15/233,245, entitled "SECURE LIMITED COMPONENTS FOR USE WITH MEDICAL DEVICES" and filed on Aug. 10, 2016, which is incorporated herein by reference in its entirety.

In various examples, the remote computing device 1204 is implemented using any of a variety of programmable devices (e.g., a device with data storage and at least one processor in data communication with the data storage). In some examples, the remote computing device 1204 includes a plurality of interfaces, one or more processors, and a data storage device coupled to one another via a communication mechanism, such as a bus. In these examples, the remote computing device 1204 also includes a battery to power the device and may include one or more antennas. The plurality of interfaces in the remote computing device 1204 include a user interface, a network interface configured to communicate with the network 1206, and a medical device interface configured to exchange information with the medical device. This information may include one or more limited functionality commands. Particular examples of the remote computing device 1204 include medical devices (e.g., in FIG. 12, medical devices other than medical device 1202), wearable devices, smart phones, tablet computers, and laptop computers. Wearable devices that may serve as the remote computing device 1204 include various garments with integrated technologies, watches, anklets, necklaces, belt buckles, and glasses.

As noted above, in examples where the remote computing device 1204 is implemented via a smart phone, a dedicated software application (or an "app") may be downloaded to the smart phone to facilitate the interactions described herein. In some examples, as an enhanced security measure, the remote computing device 1204 is configured to automatically and exclusively execute such an application when the remote computing device 1204 is connected to a power source or when the remote computing device 1204 powers up. In such examples, the smart phone operates solely as the remote computing device 1204 for enabling the communications and interactions described herein. For example, the smart phone may be configured to operate in a "kiosk mode" and display only minimal information on the user interface during such operation. For instance, the application may be written for an Android, iOS, Windows, or other operating system of the smart phone.

In some examples, the remote computing device 1204 is configured to act as an information conduit (or "hotspot") for the medical device 1202 by exchanging information regarding the medical device 1202, the patient 1210, and the environment of the medical device 1202 with a remote server 1212 via a communication network 1214. For example, in an implementation where the remote computing device 1204 is configured as an information conduit, the remote computing device 1204 is configured to pass data between the medical device 1202 and the remote server 1212 without modifying the data. In certain cases, the device 1204 may perform certain limited transformations on the data prior to relaying the data to the remote server 1212 (or to the medical device 1002 if the data is being transmitted from the remote server 1212).

In some examples, the remote computing device 1204 can establish an authenticated and secure connection over the network 1214 via another computing device (e.g., a desktop workstation, laptop workstation, tablet or other such device). For example, the user may cause the remote computing device 1204 (e.g., a smart phone) to establish a wired (e.g., USB connection) or wireless connection (e.g., BLUETOOTH connection) with the other computing device to connect to the remote server 1212.

According to some examples, the remote computing device 1204 can be configured to automatically setup communications between the medical device 1202 and the remote server 1212. In these examples, the remote computing device 1204 is further configured to display information regarding its operation and data communications via a user interface of the remote computing device 1004 but restrict user interaction with the user interface. In some implementations, the user may only be able to power on or off the device. In other implementations, the user may only be able to control screen brightness and timeouts. The operation and data communication information displayed may include battery level, connection strength to the network 1214, status of connectivity between the remote computing device 1204 and the medical device 1202 including, in some cases, status information for any ongoing communications, and version information for the hotspot component. The remote computing device 1204 may transmit the operation and data communication information to the remote server 1212. Additionally, the remote computing device 1204 may transmit information descriptive of its location to the remote server 1212 (e.g., GPS coordinates or other position/location details). In some examples, the remote computing device 1004 is configured to transmit information descriptive of the connection strength to the medical device 1202. Further, in some examples, the remote computing device 1204 is configured to establish a firewall that will inhibit any unauthorized connections to the medical device 1202. The firewall can be configured to inhibit any connections to the medical device 1202 other than through the remote computing device 1204. In some examples, the remote computing device 1204 is configured to log errors in the data storage of the remote computing device 1204 (or a storage in some other location on the network).

In some examples, the remote computing device 1204 is configured to automatically execute as a hotspot component when the remote computing device 1204 is connected to a power source or when the remote computing device 1204 powers up. Also, in these embodiments, the remote computing device 1204 is configured to exclusively execute the hotspot component. In various implementations, the remote computing device 1204, when configured as the hotspot component or otherwise, complies with 21 CFR § 880.6310 which defines a Medical Device Data System (MDDS). In one example, the remote computing device 1204 comprises hardware or software products that can be configured to transfer, store, convert formats, and display medical device data. In such examples, the remote computing device 1204 can be configured, using the techniques and systems described herein, to not modify the data, modify the display of the data, and/or control the functions or parameters of the medical device or any other medical device.

Figure 13:
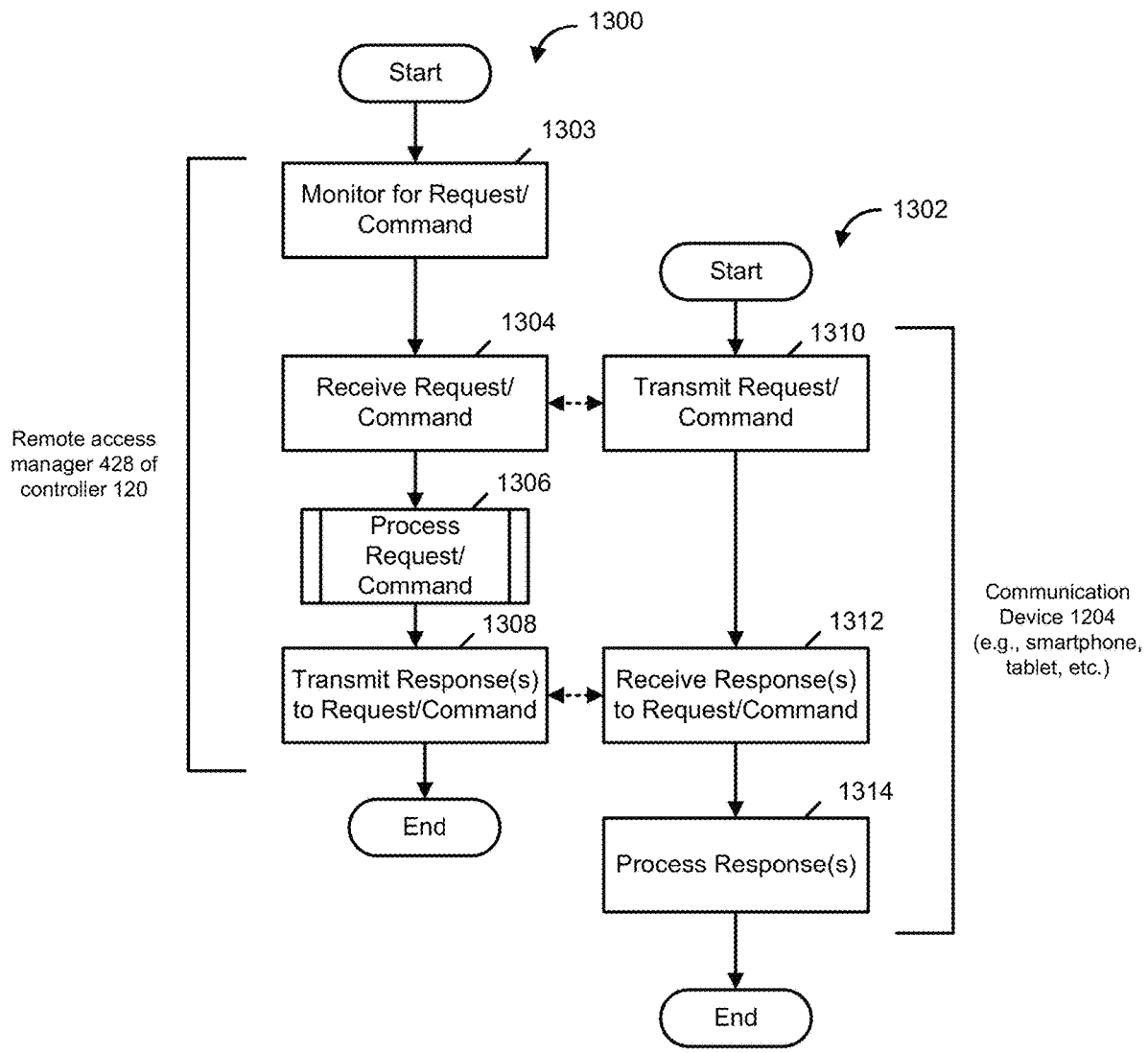
FIG. 13 shows example interface processes executed on a medical device controller and a remote computing device, in accordance with various examples of the present disclosure.

Referring now to FIG. 13, the controller 120 of a medical device 1202 can be configured to execute an interface process 1300. For instance, in one example, the interface process 1300 can be performed by the remote access manager 428 of FIG. 4, in conjunction with any other element of the medical device controller 120. A corresponding process 1302 is configured to be executed on a remote computing device 1204, e.g., a smartphone, tablet, or other personal device of the patient. For example, the interface process 300 is configured to periodically monitor (act 1303) for a request and/or a command issued from the remote computing device as discussed in detail above. Such a request may be for information regarding, e.g., an operational status of the device, results of diagnostic tests, configuration information, and/or patient information. In some cases, the request and/or command may be for the remote computing device to assert control over one or more components and/or aspects of the medical device 1202 as described herein. When executing the act of monitoring 1303, in some examples, the remote access manager 428 is configured to operate in a low power mode or a normal power mode as described in connection with FIG. 9 above. For example, the remote computing device 1204 may receive and buffer a request and/or a command from a remote system (e.g., under operation by a technician) until the remote access manager 428 polls the remote computing device 1204 for such a request and/or command. For example, such polling may occur every few minutes (e.g., every 1 minute, 5 minutes, 10 minutes, 15 minutes, etc.) for a buffered request or command. In a low power mode, the frequency may be increased to 30 minutes, 1 hour, or more. In an implementation, instead of or in addition to polling the remote computing device 1204, the medical device may poll a remote computer system or server application for such buffered commands.

In some implementations, instead of the remote access manager 428 monitoring for a request/command, the remote computing device 1204 may initiate a communication session by sending a message to the remote access manager 428. Accordingly, a push-based messaging service may be implemented in which when the remote computing device 1204 has a command and/or a request to send to the medical device, it can initiate the communication session and send the command and/or request.

In act 1310, the remote computing device 1204 transmits a request or a command to the remote access manager 428. For example, the remote computing device 1204 may interrogate or request from the medical device information concerning the device operational status, service status, device configuration, and/or patient information as described in further detail below. For example, the request or command may be any request or command from a predefined command set executable by the remote access manager 428. For example, Table 3 below lists some example commands in such a predefined command set according to at least one implementation. Additional commands also with associated descriptions may be found in U.S. Patent Application Ser. No. 15/233,245.

TABLE 3

| Command | Description |
| --- | --- |
| Request (Operational_status); Request (Service_code); | Causes the remote access manager 428 to initiate a query to one or more data sources for Operational_status of the medical device and/or associated components, systems, and subsystems. Data returned may include an operational status or fault criticality level (e.g., a Group One or a Group Two), corresponding service code(s), and corresponding actions taken on the medical device in response to the indicated operational status. |
| Request (Device_configuration) | Causes the remote access manager 428 to initiate a query to one or more data sources for device configuration information |
| Request (Patient_info) | Causes the remote access manager 428 to initiate a query to one or more data sources for patient information |
| Change (Patient_info) | Causes the remote access manager 428 to change one or more data records relating to patient information |
| Get (Element_ID) | Returns a value of the data element identified by Element_ID. |
| Set_Threshold (Value, Element_ID) | Creates an association between the specified Value and Element_ID. |
| Watch (Element_ID, Watch_Type, Report_Frequency) | Causes the remote access manager 428 to monitor the data element identified by the Element_ID according to the Watch_Type. Detected transgressions of the value of the data element will be reported to the address specified by the Watcher_Address at a frequency specified by the Report_Frequency. |
| Display_Message (Message_ID) | Causes the remote access manager 428 to request that the user interface of the medical device display a predefined message identified by the Message_ID. |
| Filter_Data (Data, Filter_ID) | Causes the remote access manager 428 to apply a filter (e.g., Low Pass, High Pass, Band Pass, Wavelet . . .) identified by the Filter_ID to the Data before transmitting the data to the remote computing device |

In act 1304, the remote access manager 428 receives the request or command from the remote computing device 1204. In act 1306, the remote access manager 428 processes the command. For example, if the command is a request for a status of a subsystem of the device, or results of a diagnostic test performed by the device, the remote access manager 428 can query appropriate data sources within the device and return the corresponding data and/or results.

In act 1308, the remote access manager 428 transmits to the remote computing device 1204 one or more responses resulting from execution of the request and/or the command and the interface process 1300 ends. As described above, depending on the command executed, the response may include information generated by or stored on the medical device. In some examples, the response includes configuration information that enables the remote computing device to receive one or more on-going transmissions of information from the remote access manager 428. These on-going transmissions may be in response to a predetermined condition, substantially in real time, during an occurrence of the predetermined condition, in response to user input, in response to a predetermined triggering event, continuous over a period of time, substantially continuous over a period of time, during periodic time intervals, or during aperiodic time intervals.

In act 1312, the remote computing device 1204 can be configured to receive the one or more responses to the request and/or command. In the act 1314, the remote computing device 1204 processes the response and the interface process 1302 ends. In some examples, the request from the remote system is a request to perform a diagnostic test, which causes the remote access manager 428 to perform a diagnostic operation in response to the request. Examples of the diagnostic test include requesting the last time a converter or capacitor has been charged or tested, or performing an audio test. In some cases, the remote access manager 428 is further configured to transmit data representing an operational status of the ambulatory medical device to the remote system. In some cases, the operational status of the controller results from performing the diagnostic test (e.g., the operational status may include the results of the diagnostic test, such as pass or fail, or the values of certain parameters that indicate whether the device is operating normally or abnormally). However, the operational status of the controller can include other information not resulting from the diagnostic test, such as device identity, run time, patient wear time, event history, alarm history, or other information that is generated by the controller. In some cases, the remote access manager is further configured to send the data representing the operational status of the ambulatory medical device in real time or substantially in real time, although it will be understood that the data can be sent at any time. For example, the diagnostic test may be performed in real time (e.g., as soon as the request is issued by the remote system and received by the device), or delayed (e.g., at some point in time after the request is issued by the remote system, such as when the request is buffered in the base station before being transmitted to the device). In some cases, the remote access manager is further configured to detect an anomalous condition of the controller, and to transmit data representing an operational status of the ambulatory medical device to the remote system in response to detecting the anomalous condition.

In some examples, the data representing the operational status of the ambulatory medical device includes a web page configured to present a virtual user interface to the ambulatory medical device via a web browser, such as shown and described above with respect to FIG. 6. For example, the data may be used to generate, in the web browser, a virtual copy or other representation of the user interface of the device to enable a patient to view and interact with the device via the remote computing device 1204 instead of the user interface of the medical device.

The request from the remote system via the remote computing device 1204 can be a request to communicate with a remote system, which establishes a communication session with the remote system via the remote computing device 1204 in response to the request. Accordingly, in some implementations, the remote access manager 428 is configured to transmit data representing an operational status of the ambulatory medical device 912 to the remote system via the remote computing device 1204. In some such cases, the remote access manager 428 is configured to detect an anomalous condition of the controller, and to transmit the data representing the operational status of the ambulatory medical device to the remote system via the remote computing device 1204 in response to detecting the anomalous condition. In some cases, the remote access manager is further configured to transmit the data representing the operational status of the ambulatory medical device in real time or substantially in real time, although it will be understood that the data can be sent at any time.

In some cases, a request from the remote system is a command to reconfigure the user interface in the event a user interface element is rendered inoperative. In such cases, the controller is further configured to reconfigure the user interface via the remote computing device 1204 to cause one of the user input elements to control another operational function instead of the original operational function of that user input element as described in detail below (e.g., see description of user interface 408).

The processes disclosed herein each depict one particular sequence of acts in a particular example. The acts included in these processes may be performed by, or using, one or more computer systems specially configured as discussed herein. Some acts are optional and, as such, may be omitted in accord with one or more examples. Additionally, the order of acts can be altered, or other acts can be added, without departing from the scope of the systems and methods discussed herein. Furthermore, as discussed above, in at least one example, the acts are performed on a particular, specially configured machine, namely a medical device configured according to the examples disclosed herein.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

What is claimed is:

1. An ambulatory medical device configured to enable remote assistance of a patient wearing the ambulatory medical device, the device comprising:
    a sensor configured to monitor a signal indicative of a physiological condition of the patient over an extended period of time;
    a network interface configured to communicate with a remote system distinct from the ambulatory medical device;
    a user interface configured for interaction with the patient;
    a controller operatively coupled to the sensor, the network interface, and the user interface, the controller configured to cause the user interface to display an ambulatory device user interface view to the patient, the ambulatory device user interface view comprising first information derived from the signal indicative of the physiological condition of the patient; and
    a remote access manager operatively coupled to the controller and configured to
        establish, via a communication session, an interaction between a remote system and the ambulatory medical device in real time or in substantially real time, and
        cause the controller to retrieve second information based on the interaction, the second information regarding the ambulatory device user interface view, as displayed to a user, and further cause the controller to provide the second information regarding the ambulatory device user interface view to the remote system.

2. The ambulatory medical device of claim 1, wherein the interaction further comprises instructions for the patient to adjust one or more electrodes of the ambulatory medical device.

3. The ambulatory medical device of claim 2, wherein the controller is further configured to transmit, to the remote system via the communication session, data representing the signal indicative of the physiological condition of the patient in response to the interaction.

4. The ambulatory medical device of claim 3, wherein the controller is further configured to transmit, via the communication session, the data representing the signal indicative of the physiological condition of the patient in response to a manual activation of a user interface element and/or in response to a remote activation, via the communication session, of the monitoring.

5. The ambulatory medical device of claim 4, wherein the interaction further comprises instructions for the patient to perform a walk test.

6. The ambulatory medical device of claim 1, wherein the physiological condition of the patient is a heart rate of the patient.

7. The ambulatory medical device of claim 1, wherein the controller is further configured to download, via the communication session, a template configured to filter noise from the signal.

8. The ambulatory medical device of claim 7, wherein the controller is further configured to activate the template without patient intervention in response to the download.

9. The ambulatory medical device of claim 7, wherein the controller is further configured to filter the noise from the signal using the template.

10. The ambulatory medical device of claim 1, wherein the controller is further configured, responsive to monitoring the signal, to display a message on the user interface and/or sound an audible cue.

11. The ambulatory medical device of claim 1, wherein the interaction includes one or more of:
   viewing an operational status of the device;
   issuing commands to the device;
   resetting the device;
   retrieving third information from the device;
   remotely viewing a local user interface of the device;
   remotely performing firmware and software updates, upgrades, or applying patches to the device;
   remotely downloading and/or applying updates to underlying treatment and/or monitoring parameters of the device;
   remotely changing threshold values for the underlying treatment and/or monitoring parameters of the device; and/or
   remotely performing a function relating to operation of the device.

12. The ambulatory medical device of claim 1, wherein the interaction includes providing to the patient, via the user interface, third information relating to a detected anomaly of the ambulatory medical device and/or a status of the ambulatory medical device.

13. The ambulatory medical device of claim 1, wherein the interaction includes providing to the patient, via the user interface, instructions for operating the ambulatory medical device.

14. The ambulatory medical device of claim 1, further comprising a textual command interface configured to enable a remote user to interact with the ambulatory medical device in real time or in substantially real time via the communication session.

15. The ambulatory medical device of claim 1, wherein the controller is configured to download a plug-in or an application via the communication session.

16. The ambulatory medical device of claim 15, wherein the plug-in or the application is configured to receive, via the communication session, instructions from the remote system.

17. The ambulatory medical device of claim 16, wherein the controller is further configured to execute the instructions in response to a command received from the remote system via the communication session.

18. The ambulatory medical device of claim 1, wherein the remote access manager is configured to allow a remote technician to guide the patient through one or more steps relating to the ambulatory medical device via the user interface.

19. The ambulatory medical device of claim 1, wherein the remote access manager is further configured to cause the controller to perform a diagnostic test in response to receiving, from the remote system and via the communication session, a command to perform the diagnostic test.

20. The ambulatory medical device of claim 1, wherein the remote access manager is further configured to transmit data representing an operational status of the ambulatory medical device to the remote system via the communication session.

21. The ambulatory medical device of claim 20, wherein the remote access manager is further configured to detect an anomalous condition of the controller, and to transmit the data representing the operational status of the ambulatory medical device to the remote system via the communication session in response to detecting the anomalous condition.

22. The ambulatory medical device of claim 1, wherein the remote access manager is further configured to cause the controller to:
   re-configure a user interface element in response to detecting an anomalous condition of the user interface element;
   re-configure a component of the ambulatory medical device in response to detecting an anomalous condition of the component; and/or
   re-configure one or more response buttons of the controller in response to detecting an anomalous condition of the one or more response buttons.

* * * * *